United States Patent [19]

Franz

[11] Patent Number: 5,423,878
[45] Date of Patent: Jun. 13, 1995

[54] CATHETER AND ASSOCIATED SYSTEM FOR PACING THE HEART

[75] Inventor: Michael Franz, Redwood City, Calif.

[73] Assignee: EP Technologies, Inc., Sunnyvale, Colo.

[21] Appl. No.: 101,335

[22] Filed: Aug. 2, 1993

Related U.S. Application Data

[60] Continuation of Ser. No. 972,870, Nov. 5, 1992, abandoned, which is a continuation of Ser. No. 861,333, Mar. 30, 1992, abandoned, which is a continuation of Ser. No. 579,801, Sep. 10, 1990, abandoned, which is a continuation-in-part of Ser. No. 225,043, Jul. 27, 1988, Pat. No. 4,979,510, which is a continuation-in-part of Ser. No. 38,974, Apr. 16, 1987, abandoned, which is a division of Ser. No. 586,697, Mar. 6, 1984, Pat. No. 4,682,603.

[51] Int. Cl.$^6$ ............................................. A61N 1/05
[52] U.S. Cl. ............................................. 607/122
[58] Field of Search ................. 607/122, 123, 125–128

[56] References Cited

U.S. PATENT DOCUMENTS

| | | |
|---|---|---|
| 1,060,665 | 5/1913 | Bell . |
| 3,665,064 | 5/1972 | Mosier et al. . |
| 4,135,518 | 1/1979 | Dutcher . |
| 4,172,451 | 10/1979 | Kline . |
| 4,365,639 | 12/1982 | Goldreyer .......................... 128/786 |
| 4,379,462 | 4/1983 | Borkan et al. . |
| 4,386,615 | 6/1983 | Sowton ............................. 128/786 |
| 4,630,611 | 12/1986 | King ................................. 128/786 |
| 4,682,603 | 7/1987 | Franz . |
| 4,690,155 | 9/1987 | Hess . |
| 4,799,474 | 1/1989 | Ueda . |
| 4,848,352 | 7/1989 | Pohndorf et al. ........... 128/419 R X |

FOREIGN PATENT DOCUMENTS

730346  4/1980  U.S.S.R. .

OTHER PUBLICATIONS

Franz et al., (1980) *Pflugeos arch.*, p. R2.
Franz et al., (1980) *Klin. Wochenschr.* 58:1357–1359.
Olsson et al., (1971) *J. Electrocardiology* 4(1) :19–23.
Ferris, *In Introduction to Bioeclectrodes*, 1974, p. 94–95.
"The Monophasic Electrogram Obtained From the Mammalian Heart" (Jochim, Katz and Mayne).
Gosling et al., "A Hand—held probe ... signals", J. Med. Eng. & Tech. (GB) vol. 3, No. 6, Nov. 1979, p. 299 (128/642).
Pepper et al., "Manual ECG Electrode", Med & Biol. Eng. & Comput., 1979, 17, 141 (128/639).
Siegel et al., "Intracardiac Electrode ... Ischemia", PACE, vol. 5 Nov–Dec. 1982, pp. 892–902 (128/642).

*Primary Examiner*—Lee S. Cohen
*Attorney, Agent, or Firm*—Ryan, Kees & Hohenfeldt

[57] ABSTRACT

The apparatus comprises a probe having a tip portion, a first electrode mounted on a terminal free end of the tip portion and a second electrode spaced along the tip portion from the first electrode for supplying a reference potential. The probe is constructed so as to hold the first electrode in contact with tissue of an in vivo beating heart with a positive pressure without causing macroscopic damage to the heart tissue while orienting the probe such that the second electrode is spaced from the heart tissue. A stylet is retractably mounted within the probe, for allowing a physician to maneuver the probe through a vein or the like. Once the probe is in position, it may be replaced by a probe of a different shape. The probe may also be retracted while being inserted, for preventing internal injury to the patient. The stylet may have a noncircular cross-section for restricting directions in which it can bend. In an alternative embodiment, a combination catheter is disclosed, including pacing electrodes for pacing the heart while measuring the potentials thereof. The pacing electrodes of this embodiment are placed near the tip of the catheter, and circumferentially displaced from one another to form an electric dipole for pacing the heart, and in addition are relatively small, to minimize the potential threshold necessary to pace the heart. Such pacing electrodes may be used without the first and second electrodes for measuring potentials.

3 Claims, 10 Drawing Sheets

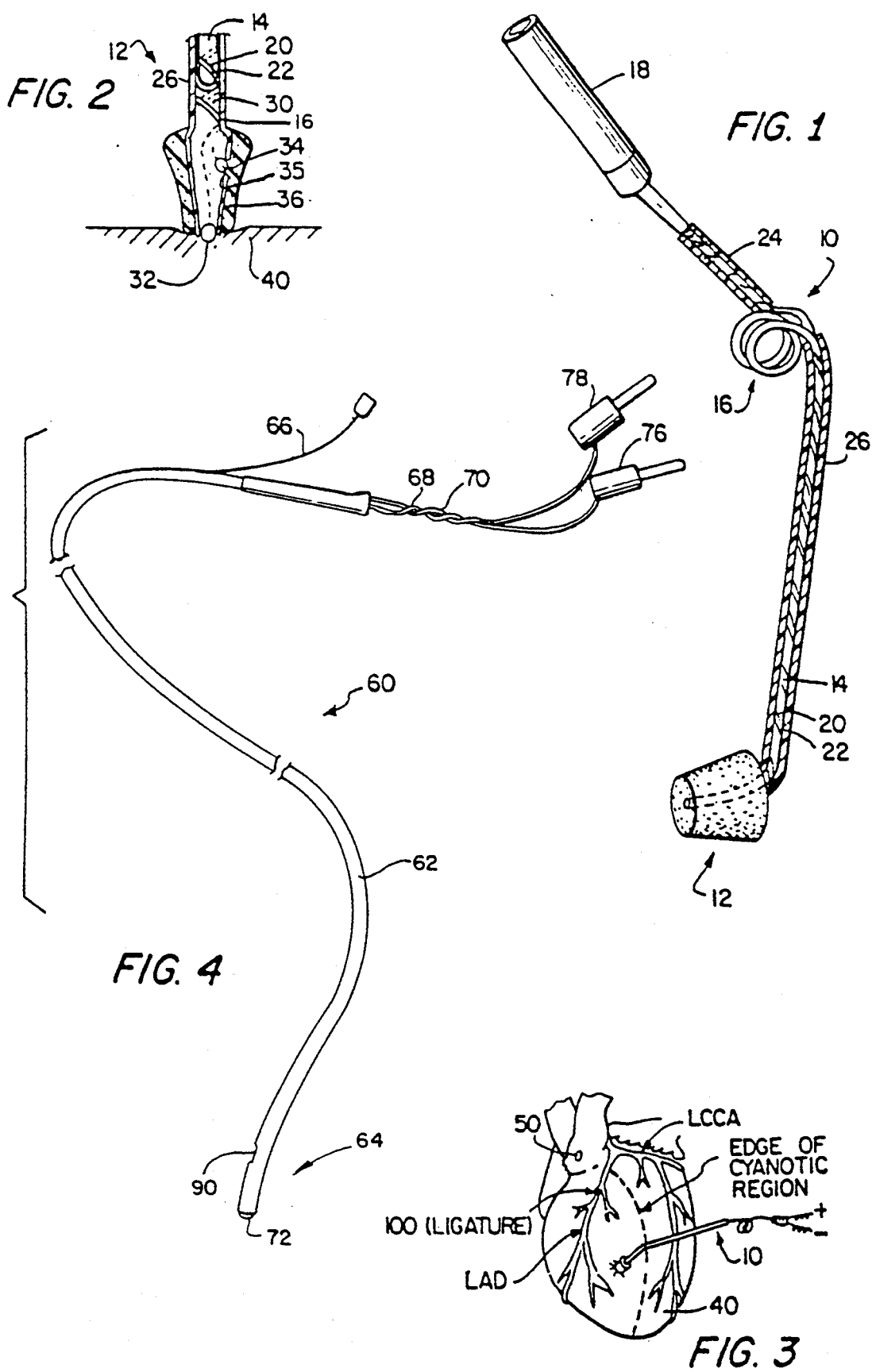

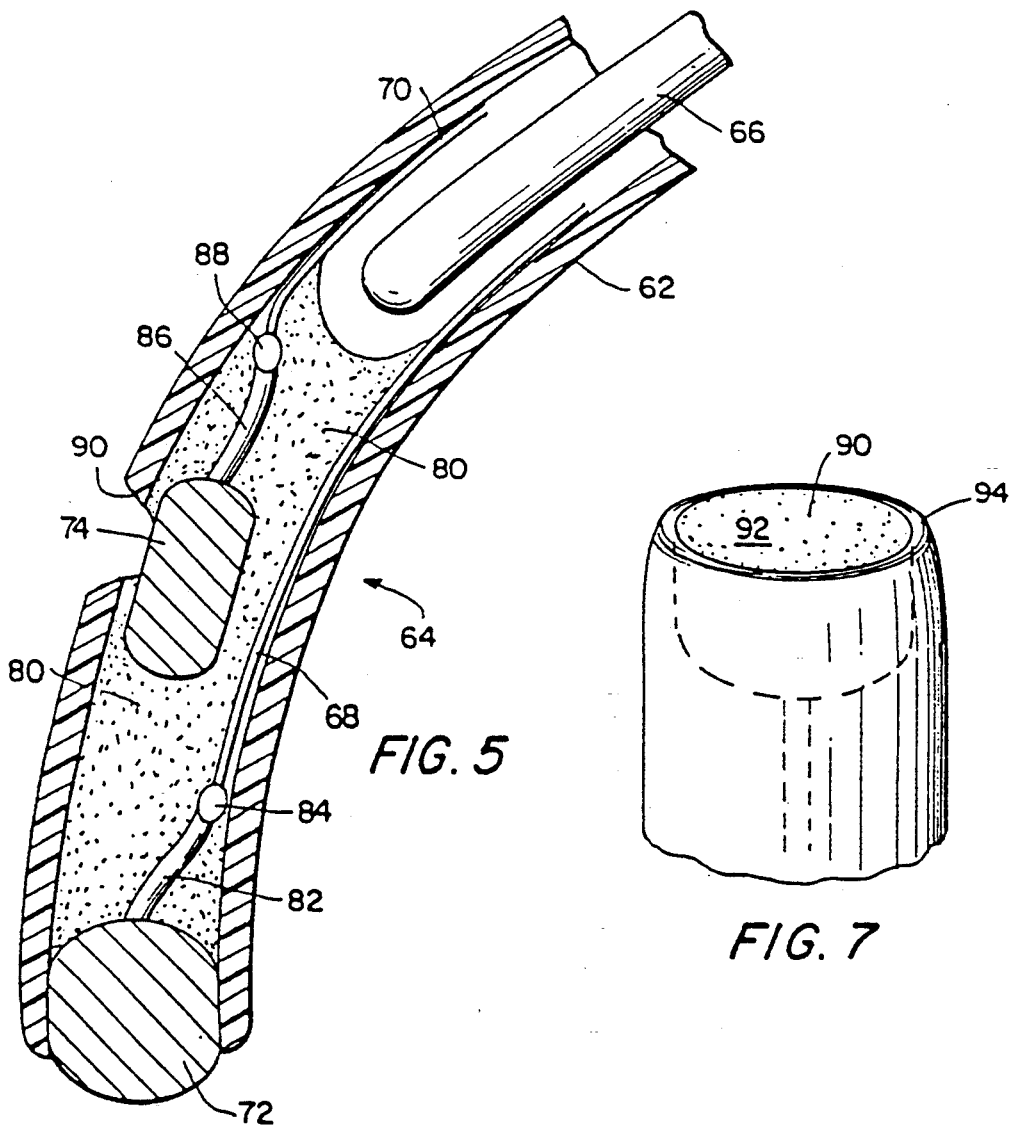
FIG. 5
FIG. 7
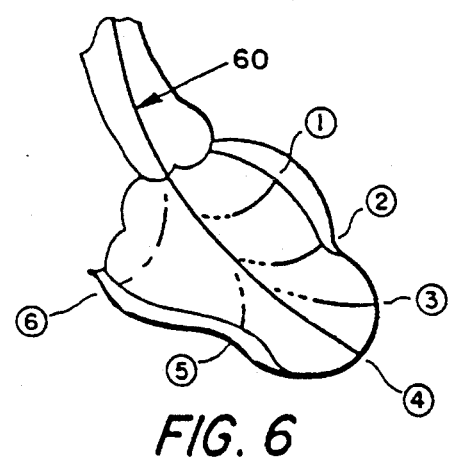
FIG. 6
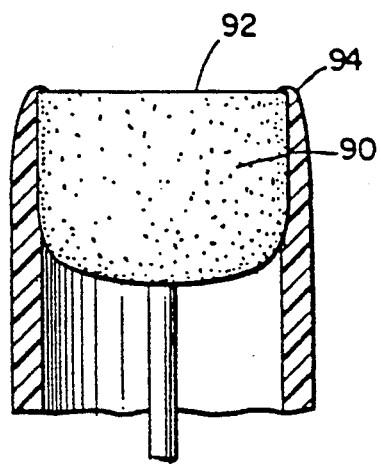
FIG. 8

FIG. 9
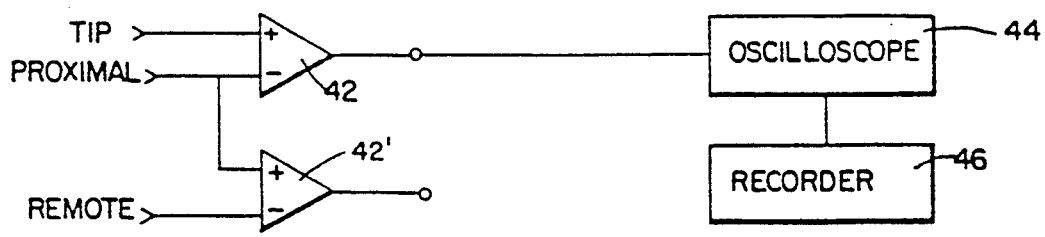
FIG. 10
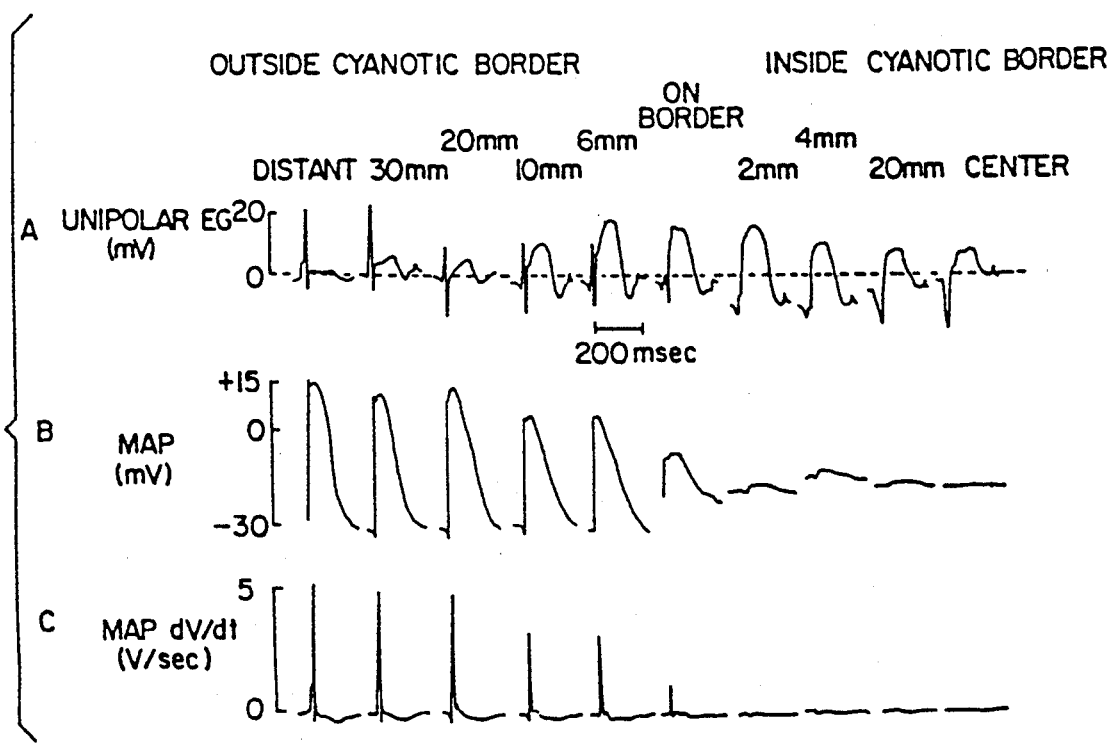
FIG. 11

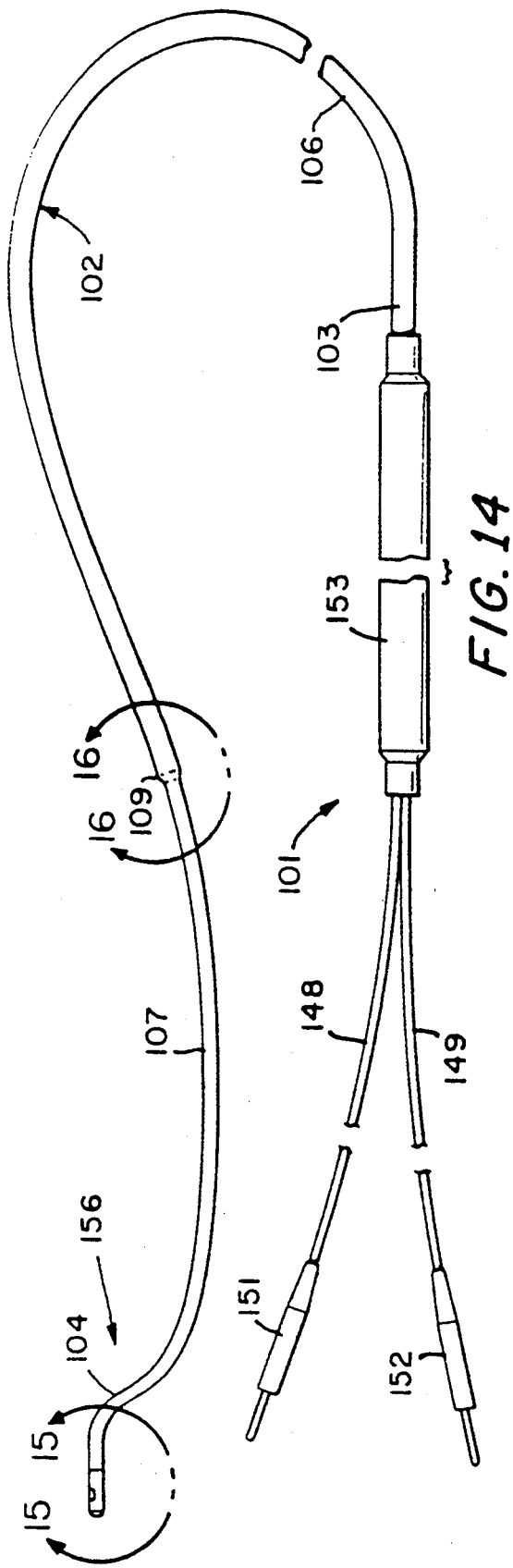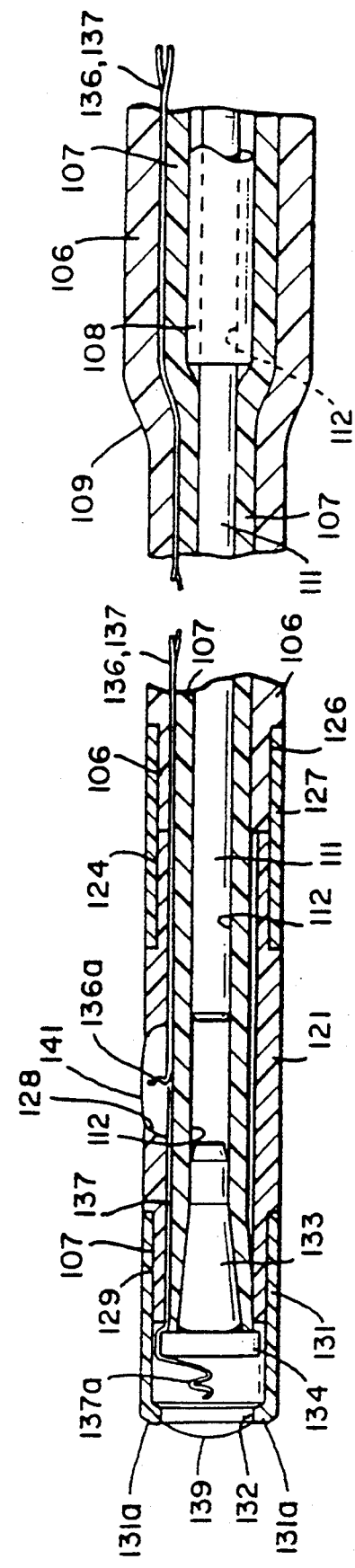

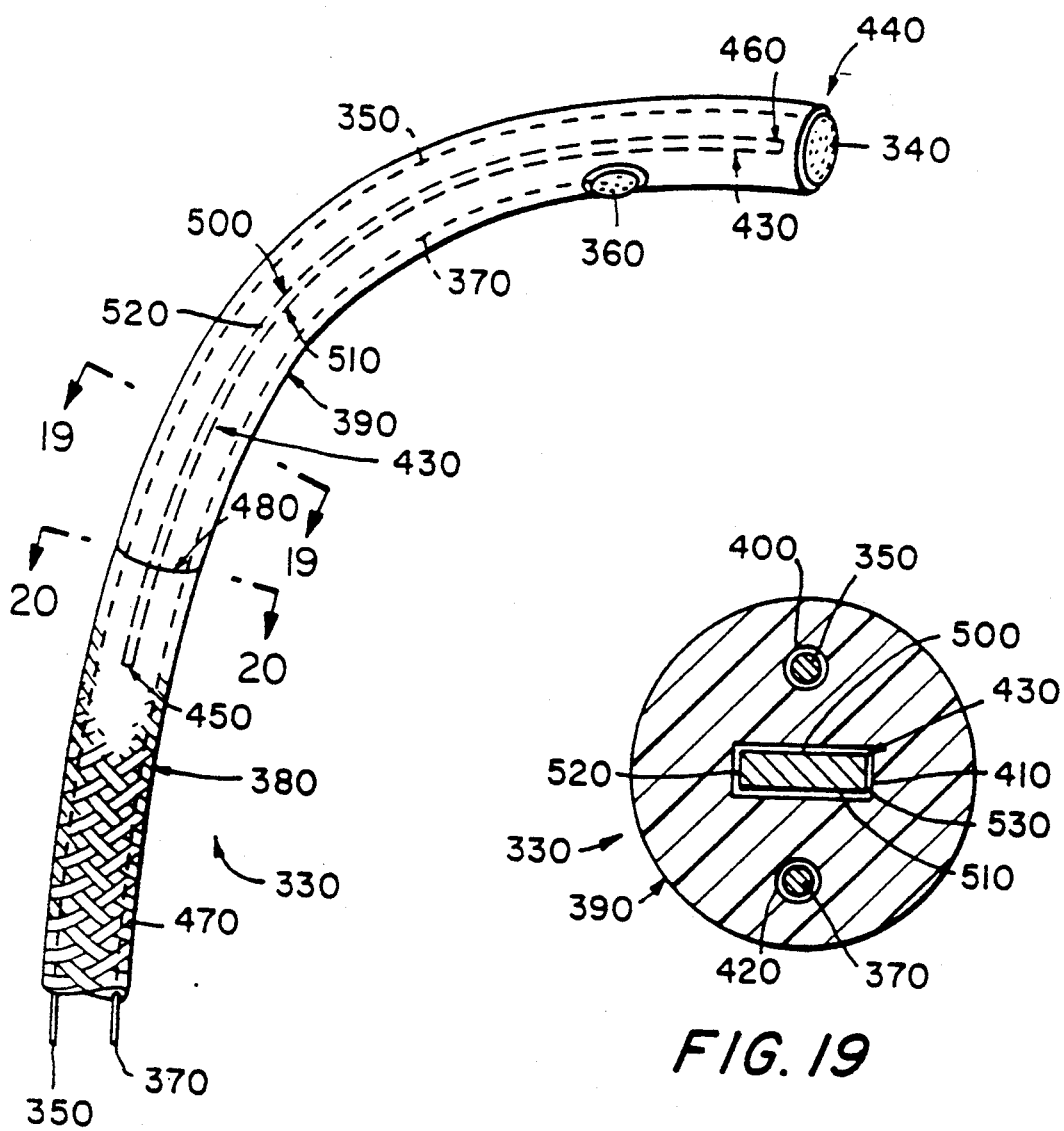
FIG. 18
FIG. 19
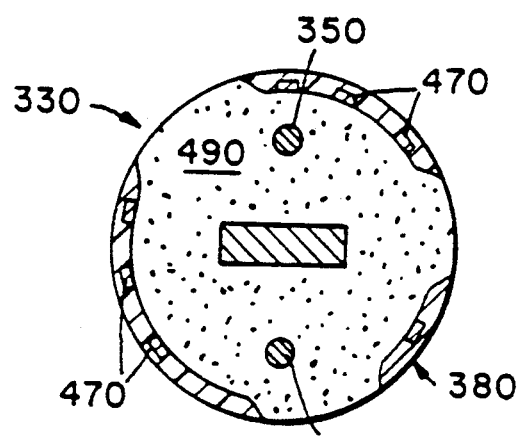
FIG. 20

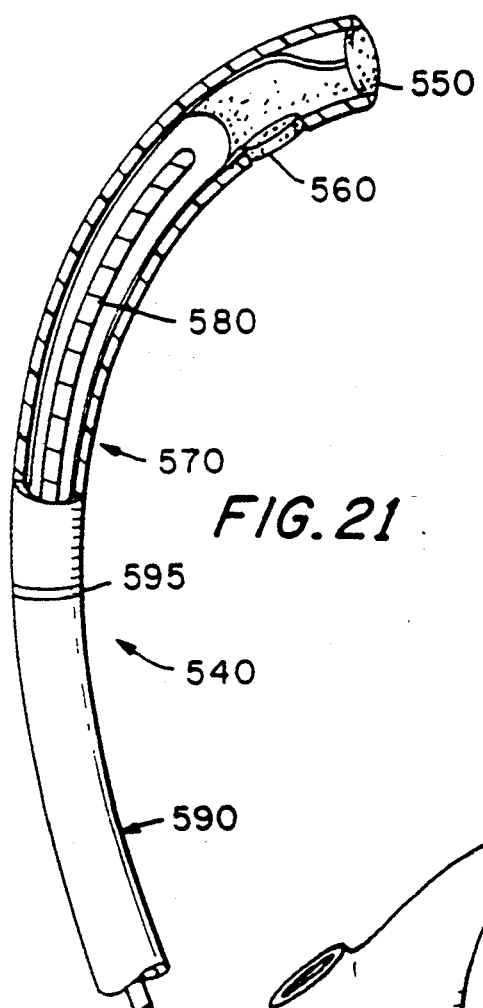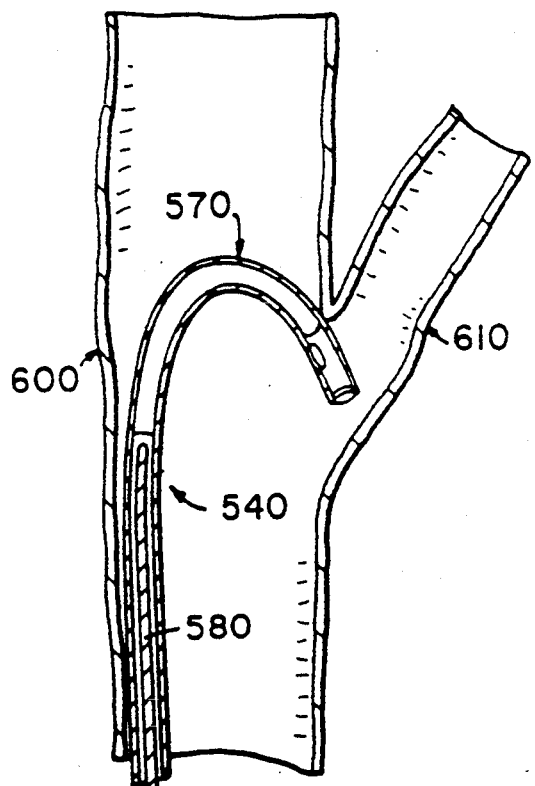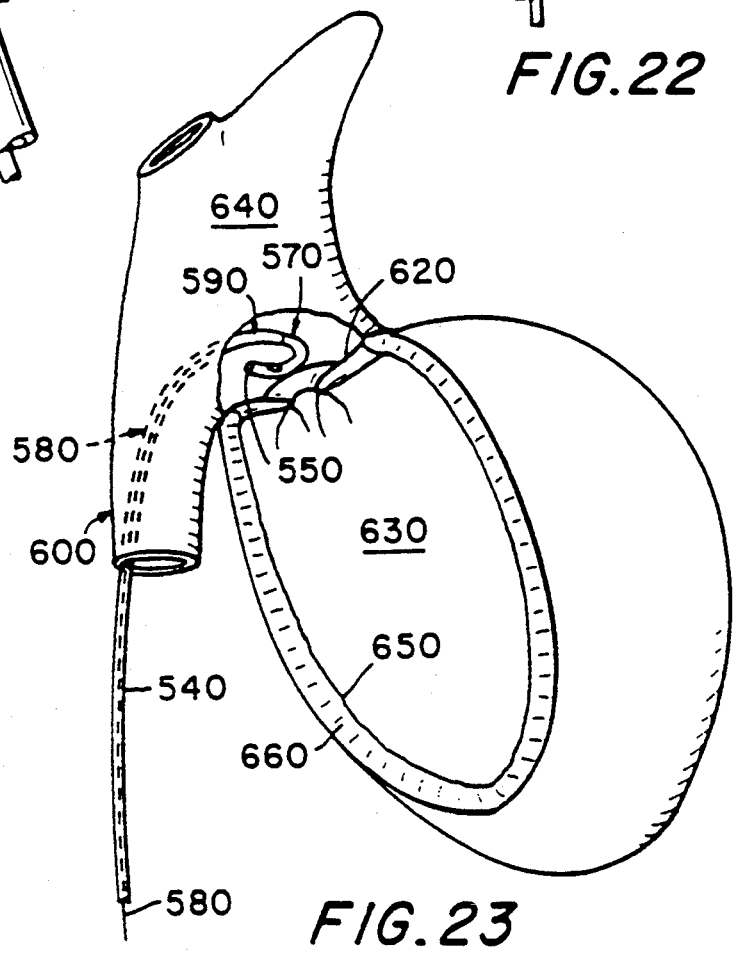

CATHETER AND ASSOCIATED SYSTEM FOR PACING THE HEART

CROSS-REFERENCE TO RELATED APPLICATIONS

This is a continuation of U.S. patent application Ser. No. 07/972,870 filed Nov. 5, 1992 (abandoned); which is a continuation of U.S. patent application Ser. No. 07/861,333 filed Mar. 30, 1992 (abandoned); which is a continuation of U.S. patent application Ser. No. 07/579,801 filed Sep. 10, 1990 (abandoned); which is a continuation-in-part of U.S. patent application Ser. No. 225,043 filed Jul. 27, 1988 (now U.S. Pat. No. 4,979,510 issued Dec. 25, 1990); which is a continuation-in-part of U.S. patent application Ser. No. 038,974 filed Apr. 16, 1987, now abandoned, which is a division of U.S. patent application Ser. No. 586,697 filed Mar. 6, 1984, now U.S. Pat. No. 4,682,603, issued Jul. 27, 1987.

This invention relates to the pacing of in vivo hearts, and more particularly to a method and apparatus for pacing a heart by contacting heart tissue with positive pressure from the tip of a catheter, and then providing pacing via electrodes displaced oppositely on a catheter in the vicinity of the catheter tip. The following disclosure is in the context of the measurement of monophasic action potentials (MAPs) within an in vivo heart, but the present invention is directed specifically to the pacing of a heart without the measurement of such MAPs. The combination of pacing and measuring the MAPs is the subject of copending U.S. patent application Ser. No. 332,875 filed Apr. 3, 1989, which is incorporated herein by reference and which is scheduled to issue on Sep. 11, 1990 as U.S. Pat. No. 4,955,382. New disclosure is included in this application, relating to the placement of the pacing electrodes near the tip of a catheter, and new FIG. 25 (discussed below) is submitted herewith to specifically show the embodiment to which the some of the present claims are directed. However, independent claim 1 and certain dependent claims are based upon the disclosure of the parent application Ser. No. 225,043, referenced above.

The text of the present application is in large part identical to that of the parent application, but for the additional text at the end relating to FIG. 25 and related text in various parts of the specification.

BACKGROUND OF THE INVENTION

Studies have been performed on tissues obtained from human hearts. It has been learned that a resting cardiac cell has a transmembrane voltage difference of about 90 mV. The inside of the cell is negative relative to the extracellular fluid and, upon cell stimulation, an action potential ensues. The action potential consists of five phases. Phase 0 is rapid depolarization, phase 1 is an early repolarization, phase 2 is the plateau phase, phase 3 is a rapid repolarization to the diastolic transmembrane voltage, and phase 4 is the diastolic period. The time-voltage course of the action potential varies among different cardiac cell types.

The electrical charge of the outer membrane of individual heart muscle cells is known as the membrane potential. During each heart beat, the membrane potential discharges (depolarizes) and then slowly recharges (repolarizes). The waveform of this periodic depolarization and repolarization is called the "transmembrane action potential." Mechanistically, the action potential is produced by a well-organized array of ionic currents across the cell membrane.

The transmembrane action potential has typically been recorded by means of microelectrodes, which are extremely fine glass capillaries that can be impaled into a single heart muscle cell. Because of the fragility of the glass capillary and the small dimensions of the heart cell, such recordings can be obtained only in small isolated tissue preparations, which are excised from animal hearts and are pinned down in a chamber with artificial solution. It is impossible to use the microelectrode technique in the intact beating heart, such as in patients.

Most of our knowledge about the electrophysiologic properties of the heart is based on the use of microelectrodes. However, because the microelectrode cannot be used in the human heart, there has been a lack of data relating to the elementary processes in the in vivo human heart, which may be different from the processes of the in vitro heart, particularly in disease.

At the turn of the century, it had already been recognized that a potential similar in shape to the later-discovered transmembrane potential could be recorded if one electrode was brought into contact with an injured spot of the heart and the other electrode with an intact spot. Those signals became known as "injury potential" or "monophasic action potentials" (MAPs) because of the waveform shape. When it was found that the injury could be produced by suction, so-called suction electrodes were developed. Thus, to examine the time course of local electrical activity under experimental conditions in which microelectrode recordings are difficult or impossible to make, such as in the vigorous beating in-situ heart, investigators have often used suction electrodes. The signal obtained with suction electrodes is monophasic and, although of smaller amplitude, accurately reflects the onset of depolarization and the entire repolarization phase of transmembrane action potentials recorded from cells in the same vicinity. Suction electrodes have also been used in human subjects, but the potential for subendocardial damage and S-T segment elevation has limited its clinical use to short recording periods of two minutes or less. Because the shape and duration of the action potentials vary from site to site in the heart, longer recording time from a single endocardial site is needed to evaluate long-term MAP changes, such as heart rate effects over several basic cycle lengths or in response to pharmacologic interventions. These longer recording times have not been achievable, however, with suction electrodes, because of the resulting damage to the tissue. Primarily for this reason, the suction electrode technique has never gained wide clinical acceptance. Therefore, the gap between microelectrode studies in excised animal tissue and what is possible in the intact human heart has remained large. There still was no safe and reliable method to obtain such signals in the human heart itself, which could provide the most valuable information, without damage to the myocardium.

Applicants herein have recognized that local heart muscle injury is not a prerequisite for the generation of MAPs, and that application of slight pressure with the tip against the inner wall of the heart would result in monophasic elevations of the signal if the filter settings were left wide open, i.e., from 0 to 5,000 Hz. Based on a theoretical evaluation of the signal modality and the factors that are responsible for its creation, applicants have found that these signals can be recorded reliably (i.e., without distortion) by using direct current (DC) coupled to amplification.

In the past, no provision has been made for measuring the electrophysiological activity of a heart in the immediate vicinity in which the heart is activated by a pacing catheter. Moreover, if it is desired to pace the heart at the same time as measuring MAPs in the heart, two entrance sites to the patient must be created and two catheters must be utilized, which is highly undesirable.

Because of the complexity of electrical cardiac activity, when a pacing electrode is inserted into the heart, and it is desired to measure the resulting action potentials of the heart, it would be of extreme usefulness to be able to measure such potentials in the vicinity of the activation, rather than at a more remote location.

Another problem to overcome is the slow DC drift caused by electrode polarization in conventional electrical material used in the recording of intracardiac electrical signals, such as silver or platinum. These materials are polarizable and cause offset and drift-which is not a problem in conventional intracardiac recordings, because those signals are AC coupled, which eliminates offset and drift. The MAPs, however, are to be recorded in DC fashion, and therefore are susceptible to electrode polarization. Applicants found that the use of a silver-silver chloride electrode material yields surprisingly good results in terms of both long-term stability of the signal and extremely low noise levels.

Another important discovery herein has been that the tip electrode of the catheter should be held against the inner surface of the heart with slight and relatively constant pressure. In order to accomplish this in a vigorously beating heart, a spring-steel stylet is inserted into a lumen of the catheter of the present invention to act as an elastic coil, keeping the tip electrode in stable contact pressure with the endocardium throughout the cardiac cycle. This leads to major improvements in signal stability.

Thus, a main feature of the catheter of the present invention is to bring into close and steady contact with the inner surface of the myocardial wall a nonpolarizable electrode which both produces and records MAPs. To achieve this property, the electrodes are formed from nonpolarizable material such as silver-silver chloride, and the tip electrode should be maintained at a relatively constant pressure against the myocardial wall, preferably with some type of spring loading. The endocardial embodiment of the catheter of the present invention contains a spring-steel guide wire which provides this high degree of elasticity or resilience which allows the catheter tip to follow the myocardial wall throughout the heartbeat without losing its contacting force and without being dislodged. The inner surface of the heart is lined with crevices and ridges (called the trabeculae carneae) and are helpful in keeping the spring-loaded catheter tip in its desired location. The contact pressure exerted by the tip electrode against the endocardial wall is strong enough to produce the amount of local myocardial depolarization required to produce the MAP. The contact pressure is, on the other hand, soft and gentle enough to avoid damaging the endocardium or the myocardium or cause other complications. In particular, no cardiac arrhythmias are observed during the application of the catheter. Usually a single extra beat occurs during the initial contact the catheter tip against the wall, when it is observed. This is a result of the stable continuous contact of the tip electrode against the heart muscle, which is provided by the spring inside the catheter shaft.

It is the tip electrode which is responsible for the generation and the recording of the MAP itself. A reference electrode, required to close the electrical circuit, is located approximately 3 to 5 mm from the tip electrode in the catheter shaft and is embedded in the wall so that it is flush with or slightly recessed in the catheter shaft, and makes contact only with the surrounding blood and not with the heart wall itself.

This reference electrode is brought into close proximity with the tip electrode, since the heart as a whole is a forceful electrical potential generator and these potentials are present everywhere in the cardiac cavities. If the reference electrode were in a remote location, then the amplifier circuit would pick up the QRS complex.

Another design feature important for the purpose of the MAP catheter is to ensure a relatively perpendicular position of the electrode tip with the endocardial wall. Again, the spring electrode is useful in this respect. Conventional catheters are usually brought into contact with the heart wall in a substantially tangential manner. Such conventional catheters are designed simply to record intercardiac electrograms, not MAPs. For the monophasic action potential catheter, direct contact of between the tip electrode and the endocardium is made. This also keeps the reference electrode, which is located along the catheter shaft, away from the heart muscle.

To facilitate the maneuverability of the catheter during a procedure in the human heart, the distal end of the catheter should be relatively flexible during the time of insertion, and the spring-loading feature preferably comes into action only after a stable position of the catheter tip has been obtained. Thus, in a preferred embodiment the catheter is constructed in such a way that the spring wire situated in the lumen of the catheter is retractable. During catheter insertion, the spring wire or stylet is withdrawn from its distal position by approximately 5 cm, making the tip relatively soft. Once the catheter is positioned, the spring wire is again advanced all the way into the catheter in order to stiffen it and to give it the elastic properties that are important for the described properties.

Important applications of the present invention are in the areas of directly studying the effects of drugs (for example, antiarrhythmia agents such as procainamide and quinidine) on the heart in real time; studying myocardial ischemia, and in particular, precisely locating areas of myocardial ischemia by studying localized MAPs; and diagnosing the nature and locality of arrhythmias originating from after-depolarizations. These after-depolarizations have hitherto been detected only in isolated animal tissue preparations where microelectrodes can be applied. The MAP catheter is a tool that can allow the clinical investigator to detect such abnormal potentials in the human heart and thereby significantly broaden our ability to diagnose this group of arrhythmias.

A field of study related to the measurement of MAPs is the actual pacing of in vivo hearts to generate such MAPs. A problem with current devices for pacing the heart lies in the fact the pacing threshold is relatively high, such that battery life for portable pacemakers is short.

SUMMARY OF THE INVENTION

Therefore, it is an object of the present invention to provide an apparatus for measuring monophasic action potentials.

A further object of the present invention is to provide a MAP measuring apparatus which can accurately record action potentials over sustained periods of time.

Another object of the present invention is to provide a MAP measuring apparatus which can measure action potentials on a vigorously beating in-situ heart.

Another object of the present invention is to provide a MAP measuring apparatus which, with slightly different modifications, may be employed to measure action potentials on both the endocardium and epicardium.

Yet another object of the present invention is to provide a method of using the apparatus for recording MAPs.

A further object of the present invention is to provide a method of detecting ischemia by sensing MAPs.

In accordance with the above objects, the present invention includes an apparatus for measuring monophasic action potentials in an in vivo beating heart. The apparatus comprises a probe having a tip portion and a first electrode mounted on a terminal end of the tip portion such that a portion of the first electrode is exposed to ambient. A second electrode is spaced along the tip portion from the first electrode for supplying a reference potential signal. The probe is provided with structure for holding the first electrode in contact with tissue of the heart with a positive pressure without causing significant macroscopic damage to the heart tissue and for orienting the probe such that the second electrode is spaced from the heart tissue.

In accordance with further aspects of the invention, a comparator is coupled to the first and second electrodes for subtracting signals received through the second electrode from the first electrode. The comparator is DC coupled to the electrodes and has a frequency response of approximately 100 kHz.

The electrodes are non-polarizable, preferably formed of silver-silver chloride, to avoid direct current drift during the course of investigation.

In accordance with further aspects of the invention, a flexible catheter may be used to hold the tip portion against heart tissue. The second electrode is exposed to ambient so as to contact fluid inside the heart. The fluid acts as a volume conductor to establish continuity between the second electrode and tissue adjacent that contacted by the first electrode. A guide wire, which may be retractable, may be disposed in the catheter to aid in directing the tip portion. The guide wire in a preferred embodiment has a rectangular or other non-circular cross-section so that resistance to bending in at least one direction is higher than the resistance to bending in another direction, for assisting in the emplacement and positional stability of the catheter.

In one embodiment, the first electrode is insulated from surrounding electrically conductive media such as blood by an insulating rim, relative to which the first electrode is recessed.

The probe may also include means for establishing electrical continuity between the electrodes and between the second electrode and tissue adjacent the tissue contacted by the first electrode. The continuity establishing means may comprise saline solution absorbed in foam material. The saline soaked foam replaces blood as a volume conductor.

The exposed surface of the first electrode may be approximately 1 mm across and the two electrodes are separated by a distance of approximately 3–5 mm.

The tip portion may also include an insulative material forming a raised ridge around the first electrode exposed portion, and the exposed portion of the first electrode may be generally planar.

In one embodiment, the catheter of the invention is provided with a material at the distal end which is more flexible than the material of the main body of the catheter. In this embodiment, the stylet may be withdrawn at least partially from the distal end, so that the catheter may be inserted past obstructions (such as the tricuspid valve or branches in the femoral vein) without damage thereto, by allowing the distal end to flex back upon itself, avoiding vascular perforation or other injury.

One embodiment of the invention includes an S-shaped distal end stiffener, which is advantageous in maintaining the desired force and substantially perpendicular position of the catheter against the endocardium.

Another embodiment of the invention provides a combination pacing and MAP catheter for very localized study of the effects of pacing activity on the heart.

In accordance with the invention, a method and apparatus are provided for determining the force with which the tip electrode of the catheter presses against the endocardium, wherein the catheter is fixed in position relative to a gram force gauge, and the distal end is placed into contact with a lever arm of the gauge, with the resulting force reading depending upon both the unstressed shape of the distal end and the stressed shape when the distal end contacts the lever arm. The force with which the electrode is actually applied to the in vivo heart strikes a balance between sufficient local depolarization of the myocardium for a good signal and avoiding damage to the heart tissue.

The method according to the present invention comprises positioning the probe such that the first electrode is held against heart tissue with a positive force and such that the second electrode is spaced from the heart tissue. The method includes comparing signals from the first electrode to reference signals from the second electrode.

According to one alternative to the method of the invention, the electrodes are short-circuited before contacting heart tissue by immersing the electrodes in a saline solution.

When the probe includes a flexible catheter, the positioning step of the method includes percutaneous catheter insertion.

The force applied to hold the first electrode in contact with heart tissue may be on the order of 20 to 50 g over the exposed area of the first electrode. A method and apparatus are provided herein whereby such force may be accurately determined, by placing the distal end of the catheter of the invention in a predetermined physical configuration against the lever arm of a force gauge.

In a particular embodiment of the present invention, pacing electrodes are provided near the tip of a catheter and are positioned opposite of one another to form dipole, both features for reducing the potential threshold necessary to pace the heart.

BRIEF DESCRIPTION OF THE DRAWINGS

The above and other objects of the present invention will become more readily understood from the following detailed description, reference being had to the accompanying drawings in which like reference numerals represent like parts throughout, and wherein:

FIG. 1 is a perspective view of a measuring apparatus of the present invention for detecting monophasic action potentials on the surface of the epicardium;

FIG. 2 is an elevational sectional view of the tip portion of the apparatus of FIG. 1;

FIG. 3 is a schematic view showing the apparatus of FIG. 1 in operation;

FIG. 4 is a perspective part sectional view showing an apparatus of the present invention for measuring monophasic action potentials on the surface of the endocardium;

FIG. 5 is an enlarged sectional view of the tip portion of the apparatus of FIG. 4;

FIG. 6 is a schematic view showing the apparatus of FIG. 4 in operation;

FIG. 7 is an enlarged view showing an improved tip electrode configuration;

FIG. 8 is an elevational sectional view of the tip electrode configuration of FIG. 7;

FIG. 9 is a schematic diagram showing the circuit connection of the apparatus of the present invention;

FIG. 10A is a graph of time versus millivolts showing actual recordings of MAPs from a non-ischemic region;

FIG. 10B is a graph of time versus millivolts showing actual recordings of unipolar DC-coupled electrograms obtained simultaneously with the recordings of FIG. 10A from a nonischemic region;

FIG. 11A is a graph of distance versus millivolts showing unipolar DC electrograms recorded at indicated distances from the visible border of cyanosis on hour after induction of ischemia/infarction;

FIG. 11B is a graph of distance versus millivolts showing monophasic action potentials taken simultaneously with the recordings of FIG. 11A;

FIG. 11C is a graph of distance versus volts per second showing the time derivatives of the monophasic action potentials of FIG. 11B;

FIG. 14 is an isometric view of another embodiment of the invention;

FIG. 15 is an enlarged cross-sectional view of the distal end of the apparatus as enclosed by the arc 15—15 in FIG. 14;

FIG. 16 is an enlarged cross-sectional view of an intermediate portion of the apparatus as enclosed by the arc 16—16 in FIG. 14;

FIG. 18 is a perspective view of an alternative distal end for the catheter of the invention;

FIG. 19 is a sectional view taken along line 19—19 of FIG. 18;

FIG. 20 is a sectional view taken along line 20—20 of FIG. 18;

FIG. 21 is a perspective view, partly in section, of an alternative embodiment to the distal end of the catheter of the invention;

FIG. 22 is a view showing the catheter of FIG. 21 in use;

FIG. 23 is another view showing the catheter of FIG. 21 in use; and

DETAILED DESCRIPTION OF THE PREFERRED EMBODIMENTS

Figure 13:
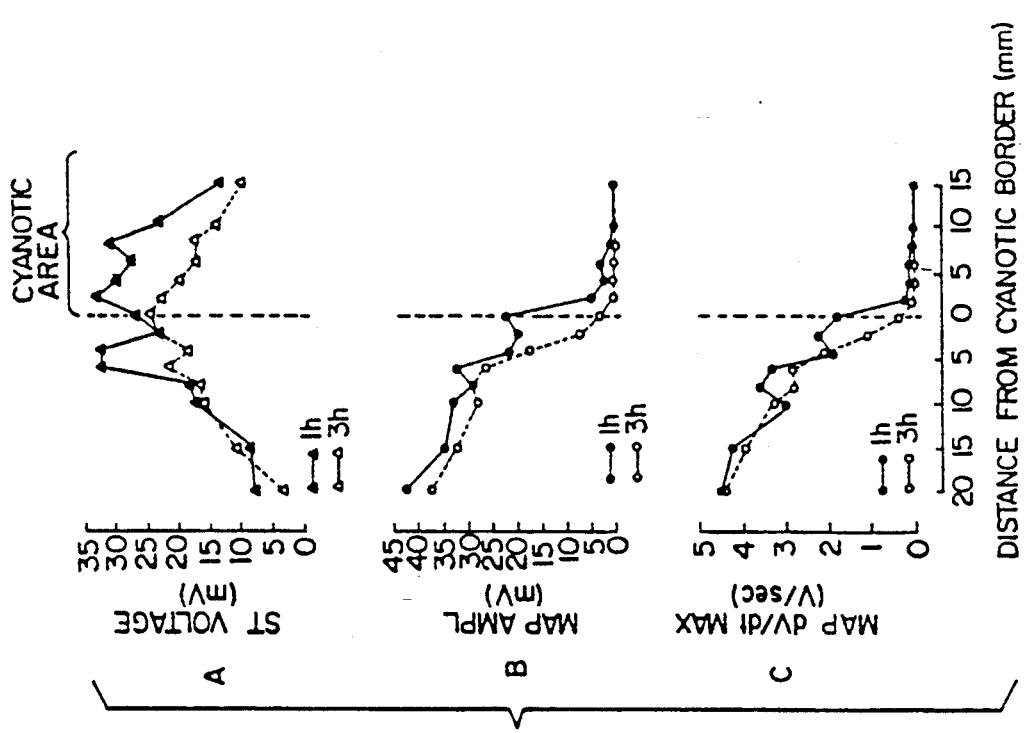
FIG. 13A is a graph of distance versus millivolts showing the effect of the duration of ischemia on S-T segment voltages recorded across a visible cyanotic border at intervals of 1 hour and 3 hours.
FIG. 13B is a graph of distance versus millivolts showing the effect of the duration of ischemia on monophasic action potential amplitudes at intervals of 1 hour and 3 hours.
FIG. 13C is a graph showing distance versus volts per second showing the effect of the duration of ischemia on maximum derivatives at intervals of 1 hour and 3 hours.

FIGS. 1 and 3 show a probe 10 according to the present invention. Probe 10 comprises a tip portion 12 which is connected to an end of a relatively stiff, flexible wire 14. The end of wire 14 attached to tip 12 is L-shaped. Wire 14 is also bent into two loops to form a spring section 16 and the opposite end of wire 14 attaches to a connector 18. A pair of electrical leads 20 and 22 are wrapped around wire 14. Leads 20 and 22 extend from the tip portion 12 to connector 18 and attach to terminals in connector 18. Connector 18 is a conventional electrical connector for making contact with leads extending to amplification and display circuitry, to be discussed hereinafter.

The portions of wire 14 above and below spring 16 are encased in plastic sheathing sections 24 and 26, respectively. Sheathing sections 24 and 26 are shown in sectional view only in FIG. 1.

Wire 14 can be conventional stainless spring steel wire which, combined with spring section 16, can produce a consistent force of approximately 20 to 30 g at the tip portion 12 when the tip portion is held against a rapidly beating in vivo heart. Sheathing 26 can be Teflon tubing or the like, and connector 18 is a conventional electrical connector which receives leads 20 and 22.

FIG. 2 shows tip portion 12 in greater detail. Wire 14 terminates part way into the tip portion. Sheathing 14 is filled with epoxy resin 30 beyond the termination of wire 14. The epoxy resin is firmly attached to wire 14 and to the sheathing. A tip electrode 32 is embedded in the epoxy resin 30 at the extreme terminus of the tip portion 12. Electrode 32 is a silver-silver chloride pellet which protrudes to form a smooth spherical surface approximately 1 mm in diameter. A proximal electrode 34 is also embedded in the epoxy resin 30 a distance of approximately 3-5 mm from the tip electrode 32 along tip portion 12. Proximal electrode 32 is also a silver-silver chloride pellet approximately 1 mm in diameter. Proximal electrode 32 is accessible through an opening 35 in sheathing 26. Electrodes 32 and 34 comprise a nonpolarizable matrix of silver-silver chloride. These electrodes are available in 1 mm pellets from In Vivo Metric Systems of California under the part no. E205.

Electrical wires 20 and 22 are connected, respectively, to electrodes 32 and 34 so as to provide electrical continuity between the electrodes and the terminals in connector 18.

Sheathing 26 is covered with a layer of foam rubber 36 which extends from above electrode 34 to a level approximately equal to electrode 32. The foam rubber is substantially cylindrically shaped and soaked with a 0.9% saline solution. The primary purpose of the foam rubber is to suspend the saline solution so as to provide electrical conductivity between proximal electrode 34 and tissue adjacent that which is contacted by tip electrode 32, as will be discussed hereinafter.

Now, with reference to FIGS. 2 and 3, an example ;of the use of probe 10 will be discussed.

Mongrel dogs weighing 20 to 30 kg were anaesthetized by intravenous injection of sodium pentobarbital (25 mg/kg) or chloralose (60 mg/kg). Respiration was maintained with room air through a cuffed entotracheal tube by a Harvard respirator. The heart was exposed through left thoractomy and suspended in a pericardial cradle.

Probe 10 was positioned against the epicardium 40 such that tip electrode 32 contacted the epicardium with a force of approximately 20–30 g while the heart beat. The force was maintained by the spring steel wire 14 and spring 16 formed in wire 14.

Epicardial MAP recordings were obtained by DC coupling the tip and proximal electrodes to a differential preamplifier 42, as shown in FIG. 9, with an input impedance of approximately $10^{11}$ ohms and a frequency range from direct current to 100 kHz. It should be noted that a preamplifier having a frequency range of direct current to approximately 5000 Hz should be sufficient for this application. The preamplified signal was displayed on a Tektronix storage oscilloscope 44 and written out on a multichannel photographic recorder 46.

The probe 10, either mounted or hand held, provided continuous MAP recordings of stable amplitude, smooth contour, and isopotential diastolic baselines over prolonged time periods from a single epicardial site. FIG. 10A shows an example of the epicardial MAP recordings. The arrow indicates the time at which contact pressure was applied. FIG. 10B shows the corresponding epicardial unipolar electrograms recorded by connecting the proximal electrode 34 of probe 10 to a second DC-coupled amplifier 42' (FIG. 9) and connecting a distant reference electrode 50 (FIG. 3) to the negative input of amplifier 42'. In FIGS. 10A and 10B, the first half of each graph was recorded at a speed of 10 mm/sec and the second half at a speed of 50 mm/sec.

The distant reference electrode 50 was provided by another silver-silver chloride electrode sewn into the aortic root. The stability of the O-reference potential of the MAP recordings was checked at the beginning of each experiment and between interventions by comparing it with the diastolic potential recorded at the aortic root.

The exact mechanism underlying the genesis of the contact electrode MAP is not clearly understood. It is theorized that the MAP recordings were obtained by exerting pressure with the tip electrode 32 against a small region of epicardium 40. This likely depolarizes a number of myocardial cells such that they are no longer capable of participating actively in regenerative depolarization and repolarization. The magnitude and direction of local current flow, which results from the potential difference between the depolarized cells under the tip electrode 32 and the adjacent normal cells would determine the amplitude and polarity of the extracellular MAP recording. The magnitude of current flow, however, may not only depend on the difference in membrane potential between cells subjacent and adjacent the electrode tip. Other factors, such as the number of cells depolarized and therefore involved in generating current flow, the degree of electrotonic coupling of cells at the boundary of interest, and the conductance in the extra- and intracellular media surrounding the recording sight are likely to influence extracellular current flow and the amplitude of the MAP.

Referring again to FIG. 2, it should be understood that the purpose of the saline soaked foam rubber 36 is to provide a conductive path between proximal electrode 34 and the epicardium 40 surrounding tip electrode 32. In other words, the foam rubber acts as an extension of proximal electrode 34 but does not pressurize the epicardium and thus does not cause depolarization of the myocardium. The actual potential being measured appears to be that between the depolarized myocardium directly beneath the tip electrode 32 and the surrounding tissue.

FIG. 4 shows a catheter 60 used for bipolar measurements of MAPs from endocardial sites. Catheter 60 has a tip portion 64 which is shown in greater detail in FIG. 5. Tip portion 64 contains a tip electrode 72 and a proximal electrode 74. Catheter 60 comprises flexible tubing 62 which may be Teflon or other durable material having a memory. Tubing 62 must be sufficiently flexible to be easily bent by the action of a beating heart, yet sufficiently resilient to maintain the tip portion 64 of the catheter in contact with the endocardium with a force estimated at approximately 20–30 g. A stainless steel guide wire 66 is inserted in the tubing 62 to improve the resiliency of the tubing and to aid in positioning the catheter tip portion 64. A pair of electrical leads 68 and 70 also extend through tubing 62 to make contact with tip electrode 72 and proximal electrode 74, respectively. The opposite ends of electrical leads 68 and 70 are connected to electrical connectors 76 and 78, respectively.

As shown in FIG. 5, tip 64 is similar to tip 12 of probe 10 except that no foam rubber is provided around the tip. Tip electrode 72, which is a sintered silver-silver chloride pellet of approximately 1 mm diameter, the same as tip electrode 32, protrudes from the terminal end of tip portion 64. Electrode 72 is held in place by epoxy cement 80, or preferably by cyanoacrylate adhesive, which has been determined to be relatively inert and biocompatible. A silver wire 82 extends from tip electrode 72 and is soldered at point 84 to insulated lead 68. Similarly, proximal electrode 74, which is spaced about 5 mm upwardly along the tip portion 64 from electrode 72, is fixed in position by epoxy 80 and is connected to a silver wire 86 which is soldered at point 88 to insulated lead 70. The proximal electrode 74 is accessible through an opening 90 in tube 62 and is recessed somewhat within the catheter so that contact is made only with the outer medium (blood) in the heart and not the endocardium.

The tip and proximal electrodes of catheter 60 are connected to a preamplifier 42 (FIG. 9) through connectors 76 and 78 to provide oscilloscope and recorded readouts of the MAPs. A remote electrode can be placed in subcutaneous tissue remote from the heat, that is, at the site of catheter insertion, to provide intracavitary electrograms.

Catheters have been employed having lengths from approximately 100–150 cm and a total outside diameter of approximately 1.3 cm. The spring steel guide wire may have a diameter of approximately 0.012–0.013 inches.

An example of the use of catheter 60 will now be set forth.

Before catheterization, electrodes 72 and 74 were immersed in sterile 0.9% saline solution for one hour with leads short-circuited to balance half-cell potentials. This procedure ensured that no appreciable direct current drift occurred during the course of the investigation. Diastolic baseline of intracavitary electrograms usually remain stable within % 1 mV during the entire recording time (1–3 hours). It should be noted that stainless steel or platinum electrodes conventionally used in clinical electrophysiology may produce considerable baseline drift of up to 160 mV during the first 30 minutes. After percutaneous catheter insertion by Seldinger technique and fluoroscopic positioning of the catheter within the heart, electrode leads were connected with sterile cables to the differential preamplifier 42. Firm approximation of the tip electrode to the endocardial surface was indicated by the recording of monophasic action potentials, which stabilized in amplitude and duration over a few beats.

FIG. 6 depicts the catheter 60 measuring MAPs at several different ventricular sites in a heart. The various sites are numbered 1 through 6 in FIG. 6. In each instance, positioning of the tip portion of the catheter was under fluoroscopic control.

FIG. 7 and 8 show an alternate embodiment of a tip electrode 90 which can be used to replace either tip electrode 32 in probe 10 or tip electrode 72 in catheter 60. Tip electrode 90 is again sintered silver-silver chloride with an exposed surface diameter of approximately 1 mm. However, the exposed surface 92 is substantially planar and is surrounded by a small ridge 94 of insulating material. This tip design has proven to be most effective in producing long-term stable recordings of monophasic action potentials. The ridge 94 aids in sealing off contact of electrode 90 from the adjacent tissue and fluid. The design o the reference electrode is as before, i.e., it is mounted along the shaft 3–5 mm proximal from the tip.

The depth ridge 94 should only be approximately 0.1 mm. The purpose of ridge 94 is to seal off electrode 90 from the surrounding tissue but not to prevent the electrode from pressurizing the myocardium. electrode 90 must both produce the pressure and sense the voltage in the pressurized tissue. If the height of ridge 94 is too great, electrode 90 will be prevented from producing adequate pressure.

Ridge 94 creates a high resistance between the pressed tissue and the surrounding tissue. The thickness of ridge 94 should also not be too great so that the electrode is close to the boundary created by the ridge.

Referring again to FIG. 1 and 4, it will be appreciated that the primary difference between probe 10 and catheter 60 is that probe 10 includes a saline soaked foam rubber piece 36. In probe 10, the saline solution acts as a volume conductor which establishes electrical continuity between the proximal electrode and the tissue surrounding the tissue pressed by tip electrode 32. With the catheter 60, the fluid (blood) within the heart itself is the volume conductor which serves this purpose. Therefore, no additional conductive material is required.

It should also be appreciated that with prior known suction electrode catheters, focal hemorrhage results at the site of suction within a few minutes. In contrast, no macroscopic damage to the tissue was seen in studies with the continuous contact electrode of the present invention. Furthermore, the stability of the contact electrode MAP over long recording periods may be considered indirect evidence that cellular alterations that lead to electrical uncoupling were minimal.

Thus, MAP recordings using the present invention appear to be safe and can easily be performed during routine cardiac catheterization along with other electrophysiologic measurements and pharmacologic interventions. MAPs recorded with the present invention can also provide a sensitive index of acute myocardial ischemia.

Identification of Ischemia/Infarction Using Monophasic Action Potentials

Figure 12:
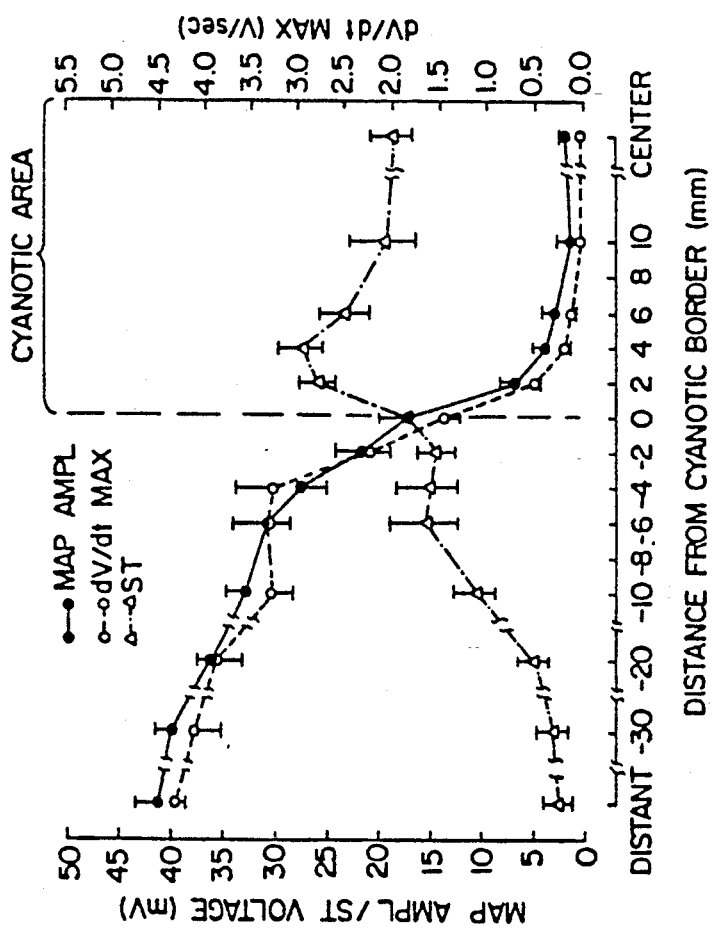
FIG. 12 is a graph of millivolts on the left and volts per second on the right versus distance showing mean values of monophasic action potential amplitudes, maximum derivatives, and total S-T segment voltages across the visible border of cyanosis from 465 recording sites in 7 dogs.

The ability to localize a region of myocardial ischemia by epicardial MAP recordings has been examined in 8 dogs and compared with standard epicardial S-T segment mapping. In order to produce transmural ischemia and infarction in a canine heart, the left anterior descending coronary artery (LAD) was permanently ligated proximal to the first diagonal branch and a biologically inert, non-resorbable polymer (dental rubber) injected into the arterial lumen. The ligation is shown on FIG. 3 at 100. This technique of vascular embolization, which extends into the arterioles, has previously been shown to create transmural infarcts with sharp histological borders in canine hearts. The white color of the injectate was also helpful in determining the vascular distribution of the LAD. Prior to ligation, 6 to 8 control measurements of the epicardial MAP and unipolar electrograms were made from defined locations inside and outside the anticipated ischemic region. Epicardial mapping was begun one hour after LAD occlusion and embolization and was completed within 15 minutes. The hand-held recording probe 10 was consecutively placed at multiple sites within, outside and near the border of the area of visible cyanosis. In each dog, measurements were made from 45 to 645 sites with an increased frequency of recordings close to the visible cyanotic border (shown in FIG. 3). The distance of the recording sites to the visible border of cyanosis was measured with a flexible ruler and recorded spatially on as map of the epicardial surface. For graphic presentation of mean data, the amplitude and dV/dt max of the MAP and the total S-T segment voltage (T-Q depression plus "true" S-T elevation) were averaged in 2 mm intervals inside and outside the visible cyanotic border. These data are shown in FIG. 12, to be discussed hereinafter.

In order to assess the effect of duration of ischemia on the electrocardiographic measurements, epicardial mapping was repeated in 2 dogs, 3 hours after coronary artery ligation and embolization, at locations similar to the mapping study performed at one hour. The data obtained are shown in FIG. 13, also to be discussed hereinafter.

In FIG. 10 are shown examples of MAP recordings (A) and standard unipolar electrograms (B) obtained from the epicardial surface of the canine left ventricle prior to ischemia. In general, MAP signals demonstrated "full" amplitude within 5 to 10 beats after stable contact of the electrode with the myocardial surface had been established. The time of contact is shown by the arrow in FIG. 10. Thereafter, MAP recordings remained stable in amplitude, $dV/dt_{max}$ and configuration for continuous recording periods of 1 hour or more.

Using non-polarizable silver-silver chloride electrodes and DC amplification, it was possible to demonstrate a negative diastolic potential and a positive systolic potential with respect to the zero reference obtained from the diastolic baseline of the epicardial surface recording measured prior to application of significant contact pressure. Total amplitude of control MAPs recorded from the left ventricular epicardial surface ranged from 35 to 55 mV (42% 4 mV, means % S.D.) which is considerably smaller than amplitudes previously reported for transmembrane action potentials (120 mV). In addition, the ratio of the positive voltage ("overshoot") to the total amplitude was greater in MAP than in intracellular recordings. The total MAP duration measured at 90% repolarization (MAPD30) was 144% 12 msec measured at a constant spontaneous heart rate of 120 % 5/min. Similar durations have been reported for transmembrane actio potentials of canine ventricular myocardium.

To further examine the precision of MAP recordings for localizing regional myocardial ischemia, epicardial MAP recordings were made with the hand-held probe 10 across the border of the regions which was made transmurally ischemic by coronary artery ligation and distal embolization with dental rubber, as discussed above. FIG. 11 shows original MAP recordings (B), their first time derivative (dV/dt) (C) and adjacent, simultaneously recorded unipolar epicardial electrograms (A) at various distances from the cyanotic border one hour after induction of transmural ischemia/infarction. MAPs recorded 20 nm or more outside the visible border of cyanosis had amplitudes, durations, configurations and $dV/dt_{max}$ values comparable to those recorded at distant sites and comparable to those recorded at the same site prior to occlusion. Epicardial MAPs recorded from sites 10 mm or less outside the cyanotic border demonstrated noticeable decreases in plateau amplitude and duration and decreases in the slope of the final repolarization phase (phase 3), resulting in a more triangular shaped MAP with a greater total duration. Values of $dV/dt_{max}$ were also noted to be decreased at these sites. As the MAP recording probe was moved across the cyanotic border, MAP amplitude decreases sharply and $dV/dt_{max}$ values approached zero 2 mm inside the border. The decrease in MAP amplitude was due to a loss in both diastolic (negative) and systolic (positive) potential. In the center of the ischemic region, nearly isopotential recordings at negative potentials ranging from $-15$ to $-5$ mV were obtained. In contrast, epicardial S-T segment voltages were highest just inside the cyanotic border decreasing progressively toward the center of the ischemic region. As seen in FIG. 11A, these increases in total S-T segment voltage were due to a combination of "true" S-T elevation and T-Q segment depression. The relative contribution of T-Q segment depression, however, was greater in recordings inside the ischemic region (where MAP recordings demonstrated markedly reduced diastolic potentials). In contrast, outside the cyanotic border, true S-T segment elevation contributed the largest portion of the total S-T segment change.

In FIG. 12 are summarized MAP and total S-T segment recordings made in 8 dogs across the lateral border of cyanosis 1 hour after induction of transmural ischemia. Unipolar epicardial electrograms demonstrating significant S-T segment elevations (27% 6 mV) were recorded 4 mm inside the cyanotic border. In epicardial electrograms recorded near the center of the ischemic region, both T-Q and S-T segment displacements were found to be lower in magnitude than those recorded just inside the border. Total S-T segment voltages in these more central ischemic regions (16–22 mV) were not significantly different in magnitude from those measured 4–6 mm outside the border (p. 13). Unipolar electrograms recorded in the center of the ischemic region did differ from those recorded just outside the border, however, by the presence of diminished R wave voltage and/or the presence of Q waves (FIG. 11). In particular, in FIG. 12, the uniform loss in MAP amplitude and dV/dt throughout the ischemic region should be noted. This is in contrast to the decline in S-T segment voltage towards the center of the ischemic region.

The distribution of blood flow across the lateral border of the cyanotic region was determined in 6 dogs using the radioactive microsphere technique. Myocardial blood flow was 1.42% 0.35 ml/min/g in the subepicardial layers and 0.65% 0.28 in the subendocardial layers 2–4 mm outside the visible edge of cyanosis and decreased to 0.01% 0.05 and 0.01% 0.02 2–4 mm inside the cyanotic border. These flow data confirm that the technique used to produce transmural infarction in a canine heart resulted in a sharp lateral border of ischemia with a transition from normal to zero blood flow over a width of only 6 mm.

The influence of the duration of ischemia on the transition of MAP and corresponding S-T segment recordings across the cyanotic border was studied in 3 additional dogs. These results are shown in FIG. 13. Measurements of MAP amplitude and $dV/dt_{max}$ repeated 2 hours after the initial mapping study demonstrated near zero values even closer to the edge of the cyanotic border than after 1 hour of ischemia as well as further reductions just outside the border. In contrast, epicardial S-T segment elevations demonstrated an overall decrease in magnitude over the same time period, making localization of the border even less well defined.

The local epicardial S-T segment voltages recorded using probe 10 are consistent with previous reports of the ability of epicardial S-T segment mapping to delineate a region of ischemia. S-T segment elevations were found 20- mm or more outside the cyanotic border and reached maximum values just inside the border. As also demonstrated in previous studies, S-T segment voltages decreased towards the center of the ischemic area such that the magnitude of S-T segment elevations recorded in the central ischemic regions was not significantly different from those recorded at sites 5 to 10 mm outside the area of reduced flow. The wide zone of transition of epicardial S-T segment voltage across the border and the loss of S-T segment voltage in the center of the ischemic region are expected on theoretical grounds. S-T segment displacements are caused by current flow between normal and ischemic myocardium. Potential gradients and thus injury current flow are less between adjacent ischemic regions than between ischemic and normal regions resulting in greater S-T segment voltages closer to the ischemic border than in the center of the ischemic area. In contrast, loss of epicardial MAP amplitude and $dV/dt_{max}$ were found to be uniform throughout the ischemic region, thus correlating better with the absence of flow.

The transition from nearly absent to nearly normal MAP recordings across the cyanotic border occurred over a distance of less than 8 mm. This electrical transition was slightly greater in width than the flow transition which had a width of approximately 6 mm. The width of the border "zone" over which transition in flow, metabolism or electrophysiologic variables are detected depends on the resolving power of the techniques employed to measure these variables. The finding of intermediate values for flow, metabolites or electrophysiological changes could result from measurements obtained either from a mixture of normal and ischemic cells or from a uniform composition of cells with an intermediate degree of change. The slightly wider transition for MAP changes, as compared to the flow transition, may indicate a limit to the resolving power of MAP recordings or may reflect scatter related to microsphere flow measurements being made from 12 mm wide tissue samples. On the other hand, abnormal MAPs recorded just outside the cyanotic border do not necessarily indicate that the tissue recorded from is injured. Current flow between ischemic and nonischemic tissue may decrease the amplitude and rise velocity of transmembrane action potentials in nonischemic cells.

A decrease in the magnitude of S-T segment voltages with duration of ischemia (see FIG. 13) has been documented in both experimental and clinical studies. It has been reported that epicardial and intramural S-T segment potentials in the porcine heart reach maximal values 7 to 15 minutes after coronary artery ligation and then decrease with time despite a progressive deterioration of the metabolic situation. Substantial reduction in S-T segment elevation in patients over the first 24 hours following acute myocardial infarction has been reported as part of the natural history of myocardial infarction. This discrepancy between S-T segment voltage and metabolic and histologic deterioration has been explained by progressive electrical uncoupling between damaged and normal myocardial cells so that, despite a persistent electrical gradient, flow of injury current decays and eventually ceases. In contrast, ischemia-induced loss of MAP amplitude and $dV/dt_{max}$ persists or becomes even more pronounced three hours after coronary artery occlusion and distal embolization than after one hour. This indicates that the information on ischemic injury obtained from MAP recordings is not compromised by electrical uncoupling as is the ECG, and suggest that MAP recordings can be used not only as a more precise but also more reliable electrophysiologic index for defining the spatial extent of ischemic-/infarcted myocardium.

In general, the apparatus and method of the present invention can be used to detect ionic imbalance due to a change in electrolyte balance in the heart as well as ischemia due to a reduction in blood flow.

Monophasic action potentials (MAPs) have hitherto mostly been recorded with suction electrodes. However, the "contact electrode" technique of the present inventio provides more stable MAP recordings than suction electrodes and has been shown to also allow safe, long-term MAP recordings in human subjects without tissue injury. Endocardial and epicardial MAP recordings using the present invention have been found to resemble transmembrane action potentials and, following the induction of regional ischemia or changes in potassium ion concentration, undergo changes similar to those previously reported in intracellular recordings. Localization of a region of myocardial ischemia by MAP mapping is more accurate and less dependent on the duration of the ischemic process than S-T segment mapping. Endocardial MAP mapping in the cardiac catheterization laboratory and both epicardial and endocardial MAP mapping in the cardiac operating room should permit the identification of sites of regional ischemia in man and to assess the acute effect of therapeutic interventions designed to reduce the severity of an ischemic insult.

In FIGS. 14, 15 and 16 there is shown another embodiment of the apparatus of the present invention for measuring monophasic action potentials in an in vivo beating heart which also can be described as an intracardiac contact electrode catheter 101 which also can be identified as a probe. The catheter 101 consists of a flexible elongate element 102 which is provided with proximal and distal extremities 103 and 104. The flexible elongate element 102 consists of an outer jacket or body 106 and an inner jacket or body 107. The outer jacket 106 and the inner jacket 107 can be formed of a suitable material as, for example, they can be formed of heat shrinkable plastic such as polyethylene. The inner jacket 107 extends over a structural reinforcing tube 108 which can be in the form of 23 gauge hypodermic needle stock formed of a suitable material such as stainless steel. The tube 108 extends from the proximal extremity 103 of the catheter 101 into a region near the distal extremity 104 of the catheter 101 as, for example, within eight centimeters of the distal extremity 104. Thus, by way of example for a catheter 101 of approximately 100 centimeters in length, the tube 108 can have a length of approximately 92 centimeters and would extend to an intermediate portion 109 as shown in FIG. 14 and 16.

An additional stiffener element 111 extends from the distal extremity 104 of the catheter as shown particularly in FIG. 15 and into the distal extremity of the tube 108. The stiffener element 111 can also be formed of a suitable material such as tempered stainless steel wire having a diameter of approximately 0.016 inches. It can extend from the distal extremity 104 as shown in FIG. 15 into a bore 112 provided in the tube 108 and can extend substantially the entire length of the catheter. The tapering of the element 111 provides a graduation in the flexibility thereof, such that the distal end of the element 111 is much more flexible than the proximal end. The tapered portion of the element 111 may be contained entirely within the S-shaped portion 156, so that the element 111 is of substantially constant diameter between its proximal end and the portion 156. It should be appreciated that the additional stiffener element 111 can be eliminated where the additional stiffness is not necessary.

A cylindrical electrode housing 121 is provided on the distal extremity of the inner jacket 107 and has its proximal extremity mated with the distal extremity of the inner jacket 106 and is secured thereto by suitable means such as an adhesive. To facilitate the making of a good bond between the housing 121 and the outer jacket 106, an annular recess 122 is provided in the distal extremity of the outer jacket 106 and an annular recess 123 is provided in the housing 121 which receive a sleeve 127 formed of a suitable material such as a polycarbonate and bonded therein by a suitable adhesive.

An ovoid recess 128 is formed in the housing 121 and is approximately 0.064 inches in length, and 0.046 inches in width. The distal extremity of the housing 121 is provided with an annular recess 129 which receives the proximal extremity of a cylindrical tip retainer 131 formed of a suitable material such as a polycarbonate and retained therein by suitable means such as an adhesive. A forwardly facing opening 132 is provided in the retainer 131. A conical type wedge 133 having a head 134 is seated in the bore 112 and expands the distal extremity of the inner jacket 107 so that it tightly engages the tip retainer 131 to provide a press fit.

The retainer 131 preferably includes a rim 131a which defines the opening 132 and protrudes slightly beyond the edge of the tip electrode 139. With this design, when the tip electrode is in place against an endocardial site, the rim 131a contacts the endocardium surrounding the site, and so prevents the tip electrode 139 from making electrical contact with blood within the heart. As can be seen, the side electrode 141 is thus dimensioned so that it is slightly recessed within the recess 128 so that the outer periphery of the side electrode 141 is surrounded by the insulating material of the rim 131a which can provide a seal between the side electrode 141 and the blood. This ensures that the tip electrode is electrically isolated from the side electrode 141, which produces accurate and reliable MAP readings.

A pair of electrical conductors 136 and 137 which can be formed of a suitable material such as insulated copper are provided which serve as signal wires. The conductors 136 and 137 are provided with S-shaped terminal portions 136a and 137a respectively which are embedded in a suitable conducting material to form electrical contact therewith to provide a tip electrode 139 and a side electrode 141. It has been found to be preferable to form the tip and side electrodes 139 and 141 by utilizing a silver-based conductive epoxy or other binder and adding to that approximately 20% by weight silver-silver chloride which has been found to provide a stable offset potential for a period in excess of one or two hours.

A particularly suitable structure for the electrodes 139 and 141 is provided by utilizing silver-silver chloride flakes (rather than powder) bound together by cyanoacrylate adhesive. This will produce a particularly conductive electrode, and the cyanoacrylate is a relatively inert and strong binder which is biocompatible.

It has been found such an electrode matrix has been particularly satisfactory in that it makes it relatively easy to manufacture the tip electrodes. After the tip electrodes are in place, they are machined to the desired conformation, for example, the convex shape for the side electrode 141. It is believed that this machining is also advantageous because in addition to shaping the electrode it exposes the silver-silver chloride crystals so that they come in direct contact with the heart during use of the apparatus or device as hereinafter described. The material can be molded and pressed around the S-shaped tips 136a and 137a of the conductors 136 and 137 thereafter permitting the conductive binder to harden in place. It has been found that it is desirable to place the side electrode 141 proximal of the tip electrode 139 by a suitable distance as, for example, 3 to 5 millimeters.

The conductors 136 and 137 are connected at their proximal extremities to conductive flexible insulated leads 148 and 149 that terminate in adaptors 151 and 152 respectively. A sleeve 153 formed of a suitable material such as a heat shrinkable plastic is mounted on the proximal extremity 103 of the catheter 101 and encapsulates the connections made (not shown) between the leads 148 and 149 and the conductors 136 and 137.

As can be seen particularly in FIG. 14, a gentle S-shaped bend or curvature 156 is provided in the proximal extremity of the catheter 101 which serves to provide the springiness desired to maintain the tip electrode 139 in contact with the heart muscle during the time that the heart is beating. As explained in connection with the previous embodiments, it is desirable that the catheter electrode housing 121 be disposed in a direction which is substantially perpendicular to the point at which the catheter engages the heart muscle which permits the tip electrode 139 to engage the surface of the heart and to leave the side electrode 146 free in the blood medium. This ensures that there will be no short circuit between the electrodes except through the blood which serves as the conducting medium. The S-shaped curvature 156 is important in that it facilitates proper alignment of the distal extremity of the catheter 101 with the heart so that the perpendicularity hereinbefore described is obtained. In addition, the S-shaped bend 156 provides a certain amount of resilience that ensures that a substantially constant contact pressure is provided against the endocardium while the heart beats.

Thus, it can be seen that with the present invention a catheter has been provided which can be pressed against the heart with a force and position which remain substantially constant even while the heart is beating. The S-shaped bend is like an elastic spring to accommodate the movement of the beating heart while at the same time maintaining a substantially constant pressure on the heart so that accurate and precise signals can be obtained by the electrodes to make it possible to record stable signals over relatively long periods of time as, for example, one to two hours.

Figure 17:
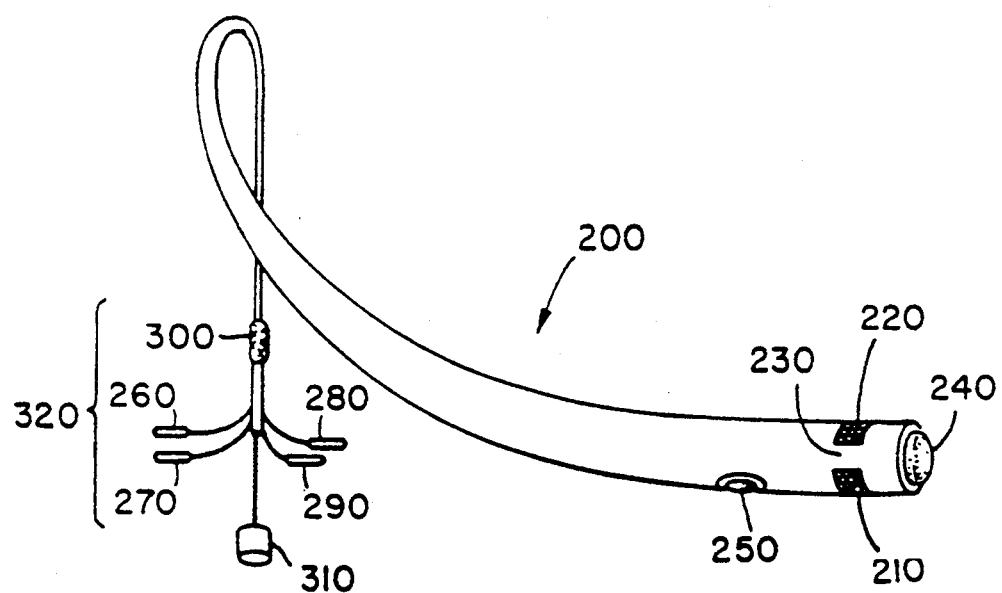
FIG. 17 is a perspective view of another embodiment of the present invention.

FIG. 17 shows an alternative embodiment of the invention, depicting a catheter 200 which is a combination pacing catheter and MAP catheter. Thus, the new combination catheter 200 has been arrived at, in which pacing electrodes 210 and 220 are mounted at the distal end 230 of the catheter 200. In addition, a tip electrode 240 and a side electrode 250 are provided, as in the configuration of FIG. 5, and are electrically connected to connections such as plugs 260 and 270, respectively.

The pacing electrodes 210 and 220 are similarly connected to plugs 280 and 290, respectively. Plugs 280 and 290 are standard plugs. The method of use of pacing electrodes such as electrodes 210 and 220 for activating is well known in the art in standard configurations pacing electrode catheters; that is, the same types of electrical signals which are provided to pacing electrodes in standard pacing catheters may also be provided to the electrodes 210 and 220 in the present invention. It will be understood that contained within FIG. 17 are the necessary electrical leads to the electrodes 210, 220, 240 and 250, and in addition stylets and other features as described herein with respect to other embodiments may be included.

A coupling 300 for the plugs 260-290 is provided, insuring a reliable connection between the plugs to the electrical leads contained within the catheter 200. This coupling 300 is preferably of a hard material such as polycarbonate, and has an enlarged diameter relative to the catheter 200. This provides greater torque control for the user of the catheter when manipulating the catheter into the heart and positioning the tip electrode 240 against the endocardium.

In addition to the coupling 300, a knurled knob 310 may be attached at the proximal end 320 of the catheter 200. The knob 310 is preferably connected to the catheter 200 in a nonrotatable fashion, such that axial rotation of the knob 310 causes similar axial rotation of the catheter 200. As shown in FIG. 17, the knob 310 may be generally cylindrical in configuration, or may be of some other convenient shape for twisting by hand.

In the preferred embodiment, the electrode 210 is located 2-6 mm from the tip 230. The other electrode 220 is also located 2-6 mm from the tip 240. As shown in the preferred embodiment, the distances between the tip 240 and the electrode 210 is substantially equal to the distance between the electrode 220 and the tip 240. Also, in the preferred embodiment, the electrodes 210/220 range in size from about 1-3 mm.

Figure 17A:
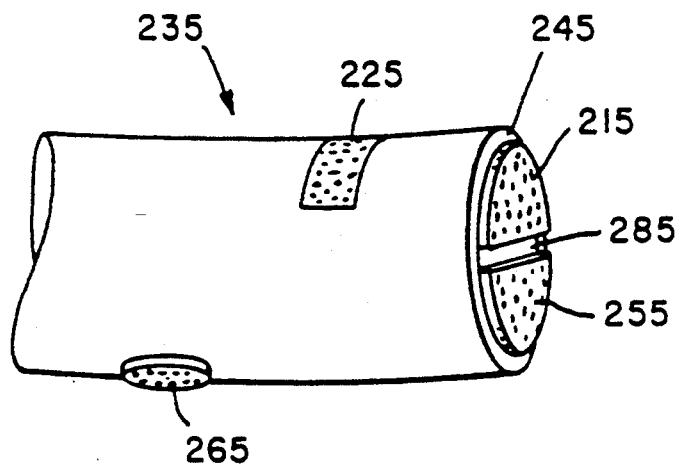
FIG. 17A an enlarged view of an alternative embodiment of the distal end of the apparatus of FIG. 17.

An alternative embodiment for the distal end 230 of the catheter 200 is shown as distal end 235 in FIG. 17A. In this embodiment, two pacing electrodes (which are typically made from platinum) 215 and 225 are provided, with the pacing electrode 215 being disposed at the tip 245 of the distal end 235. In this embodiment, the tip electrode 255 is reduced in size (relative to the tip electrode 240), but the side electrode 255 is the same as in the configuration shown in FIG. 17. As with the FIG. 17 embodiment, each of the electrodes 215, 225, 255, and 265 shown in FIG. 17A includes its own electrical connection to a plug at the proximal end of the catheter.

A distinct advantage of the configuration of FIG. 17A is that the pacing electrode 215 is positioned directly adjacent the tip electrode 255. As mentioned above, devices presently available are unable to provide pacing in the immediate vicinity of action potential measuring, and both the configurations of FIG. 17 and FIG. 17A for the first time provide such capability. In FIG. 17, the pacing electrodes 210 and 220 are preferably disposed as close to the tip electrode 240 as possible, with the configuration of FIG. 17A allowing the electrodes 215 and 255 to be extremely close, separated only by a layer of insulation 285, such as would separate two lumens in a catheter. Thus, pacing may be provided in the same area of myocardium as action potential measurement, providing a new and heretofore unavailable method of measuring the heart's reaction to pacemaking.

One particularly useful advantage to the combination pacing/MAP catheter is in determining the effective refractory period of the heart, i.e. the longest interval between two separate stimuli to the heart where the second stimulus fails to energize the heart. In other words, the effective refractory period is the time required by the heart to recover from the effects of depolarization. There is a correlation between the effective refractory period (which may be on the order of 250 ms) and the action potential, and both of these may vary significantly from site to site within the heart. Thus, an important application of the combination catheter 200 is to detect the correlation between the effective refractory period and the MAPs generated for specific locations in the heart. Such an application is described in detail in the article by M. Franz (one of applicants herein) and A. Costard entitled "Frequency-dependent effects of quinidine on the relationship between action potential duration and refractoriness in the canine heart in situ," *Circulation* 77, No. 5, 1177-1184, 1988, which is incorporated herein by reference. It will be noted that this article describes such a method utilizing two electrodes; however, the embodiment of the current invention involving four electrodes (as in FIGS. 17 and 17A) also enables the use of such a method, and it is advantageous to use separate, slightly spaced, electrodes for the pacing electrodes and the MAP electrodes, respectively.

Another alternative embodiment to the invention is shown in FIGS. 18-20. In this embodiment, a catheter 330 is provided of a configuration similar to that described with respect to the other embodiments herein, including a tip electrode 340 with its electrical connection 350, and a side electrode 360 with its electrical connection 370. The catheter 330 is formed from two different materials, with a main section 380 formed from a relatively stiff material such as polyurethane, and a tip section 390 formed from a softer material, such as the PELLETHANE 2363-80A (trademark) polyurethane product produced by Dow Chemical.

The tip portion 390 is preferably of a substantially solid cross-section, as shown in FIG. 19, with three lumens 400, 410 and 420 there through. As shown in FIG. 19, lumens 400 and 420 are generally circular in cross-section to accommodate the electrical connections or leads 350 and 370. Other cross-sectional shapes for the lumen 400 and 420 are acceptable, so long as they accommodate the cross-sectional shapes of the connections 350 and 370.

The lumen 410 is noncircular in cross-sections, and in the preferred embodiment is substantially rectangular. An elastic stiffener 430 is provided, and extends through the lumen 410 from the distal end of the tip section 390 to the main section 380. The elastic 430 may comprise a metal ribbon or other material which may be permanently bent into a desired configuration and have the characteristics of elasticity of springiness, so that when the distal end 440 of the catheter 320 is pressed upon slightly, the ribbon 430 will bend, but will spring back to its original shape upon release. However, more substantial pressure on the distal end 440 i.e., bending the ribbon 430 such that the arc described between its first end 450 and its second end 460 changes substantially, will cause the ribbon 430 to deform into a different shape as desired by a physician or other user of the catheter 330.

The main section 380 of the catheter 330 preferably includes a metal braid 470 integrally formed or otherwise carried within the polyurethane material, as shown in FIGS. 18 and 20. The section 380 may be formed in a standard manner from two concentric tubes (not separately shown) of polyurethane, with the braid 470 placed into position in the outer tube, and the inner tube then extruded in position within the braid 470.

The main section 380 is attached to the tip section 390 at a junction 480 by means of an adhesive 490, shown in FIG. 20. The first end 450 of the elastic stiffener 430 preferably extends a short distance into the main section 380, and enough adhesive 490 is provided both to bind and seal the ends of the sections 380 and 390 where they abut one another at the junction 480 and to extend from the junction 480 to the first end 450 of the stiffener 430, providing a secure adhesion between the stiffener and the electrical connections 350 and 370, on the one hand, and the main section 380, on the other hand. The adhesive 490, which may be epoxy, cyanoacrylate-related adhesive, or some other appropriate adhesive, when hardened, also serves to stabilize the first end 450 of the stiffener 430, in effect anchoring it relative to the main section 380.

In order to use the catheter 330, a physician first bends the tip end 390 into the configuration he desires. It has been found that a generally C-shaped tip end is useful for maneuverability. The curvature of the arc between the first and second end 450 and 460 of the stiffener 430 may be greater or less, depending upon the size of the patient. The tip 390 should be bent such that the stiffener 430 describes the resultant arc along its longer surfaces 500 and 510, rather than along its shorter surfaces 520 and 530. That is, from the point of view of FIG. 18, the surface 520 is parallel to the plane of the paper, whereas surfaces 500 and 510 are perpendicular to the plane of the paper. The surfaces 520 and 530 thus lie in parallel planes, whereas the broader surfaces 500 and 510 described the arc between first and second 450 and 460 of the stiffener 430. This is highly advantageous for torque control of the catheter 330 when manipulating it into position. This is because the resistance to bending is much less if the bend is made along the surfaces 500 and 510 (such as in FIG. 18) vis-a-vis the bend being made along the narrower surfaces 520 and 530. As with the other embodiments herein, the catheter 330 is radiopaque, and a fluoroscope is used to position the distal end 440 within the heart. With the configuration of FIGS. 18–20, it is very easy to predict how the tip section 390 will bend as it meets obstructions or vascular junctions while it is being positioned. This greatly increases the ease with which the physician may position the catheter 330, and in addition assists the physician in positioning the distal end 440 against the endocardium for MAP measurements.

FIGS. 21–23 show another embodiment of the invention, comprising a catheter 540, with, as in the other embodiments described herein, a tip electrode 550 and a side electrode 560 electrically connected to plugs (not separately shown) at a proximal end of catheter 540. As with the embodiment shown in FIG. 5, the catheter 540 has a tip portion 570 and a guide wire or stylet 580, which is retractable. The catheter 540 also includes a main portion 590, which is made from a flexible material such as polyurethane. The tip portion 570 is also from a flexible material, but the materials for tip portions 570 and 590 are chosen such that the main portion 590 is considerably stiffer than the tip portion 570. The main portion 590 is connected to the tip portion 570 by means of a biocompatible adhesive 595.

The catheter 540 is utilized as follows: the stylet 580, which is controlled from the proximal end of the catheter 540, is placed in its most distal position, as shown in FIG. 21. A curvature is chosen by the physician and provided to the distal end of the guide wire 580, much as with the stiffener 430 shown in FIG. 18. The catheter 540 is then maneuvered into the body, such as through the femoral vein. Observing the catheter through a fluoroscope, the physician may maneuver it up into the inferior vena cava, as shown in FIG. 22. When a vascular junction is reached, such as the junction between the hepatic vein and the inferior vena cava 600, as depicted in FIG. 22, the physician has the option of retracting the stylet 580, as shown in FIG. 22. The material of the tip portion 570 is flexible enough so that it will readily bend over into a bight without damaging or perforating the vascular tissue. Once past such an obstruction, the physician then has the option of replacing the stylet 580 at its most distal position.

FIG. 23 shows a very important use for this embodiment of the invention. Once the catheter 540 has reached the tricuspid valve 620 to the right ventrical 630, the stylet 580 is retracted out of the tip portion 570. Thus, the tip portion 570 is inserted into the right atrium 640, and may be pressed against the tricuspid valve 620 without damage thereto, since the tip portion 570 is soft and flexible. As the tricuspid valve opens, the tip portion 570 then springs back into position, such that its distal end enters the right ventricle 630. At that point, the catheter 540 may be pushed further into the right ventricle 630, and the tip electrode may then be positioned against the endocardium 650 for making MAP measurements from the endocardium 650 and the myocardium 660. At this point, the physician may withdraw the guide wire or stylet 580 entirely, and may insert a different guide wire, such as the stiffener element 111 depicted in FIG. 15, with its S-shaped distal end 156 (shown in FIG. 14 from outside the catheter). As discussed above, the S-shaped curvature is very useful in maintaining the tip of the catheter (such as at electrode 550, shown in FIG. 23) against the endocardium, and for providing the proper resilience or springiness to maintain contact with the endocardium as the heart beats.

The force with which the tip of the catheter of the present invention presses against the endocardium is optimally within the range of 20–50 g of force. This force is arrived at by balancing two competing considerations. The first of these is that the tip electrode (such as tip electrode 340 of the catheter 330 shown in FIG. 18) should contact the endocardium sufficiently strongly that the myocardial cells in the vicinity of the tip electrode 340 are depolarized in a reliable fashion. Balanced against this is the consideration that the tip electrode 340 must not penetrate or damage the mycocardium.

A highly useful application for each of the embodiments discussed herein, such as the embodiments of FIGS. 14–23, is in the area of disease diagnosis, in particular in the measuring of drug effect (such as antiarrhythmia drugs) on the heart and in other diagnostic uses, such as measuring the reaction of the myocardium to varying types of signals provided to the pacing electrodes. Such applications are discussed in the article by E. Platia, M. Weisfeldt and M. Franz (applicant herein) entitled "Immediate Quantitation of Antiarrhythmic Drug Effect by Monophasic Action Potential Recording in Coronary Artery Disease," *Am. J. Cardiology* 1988; 61; 1284–1287, which is incorporated herein by reference.

Figure 24:
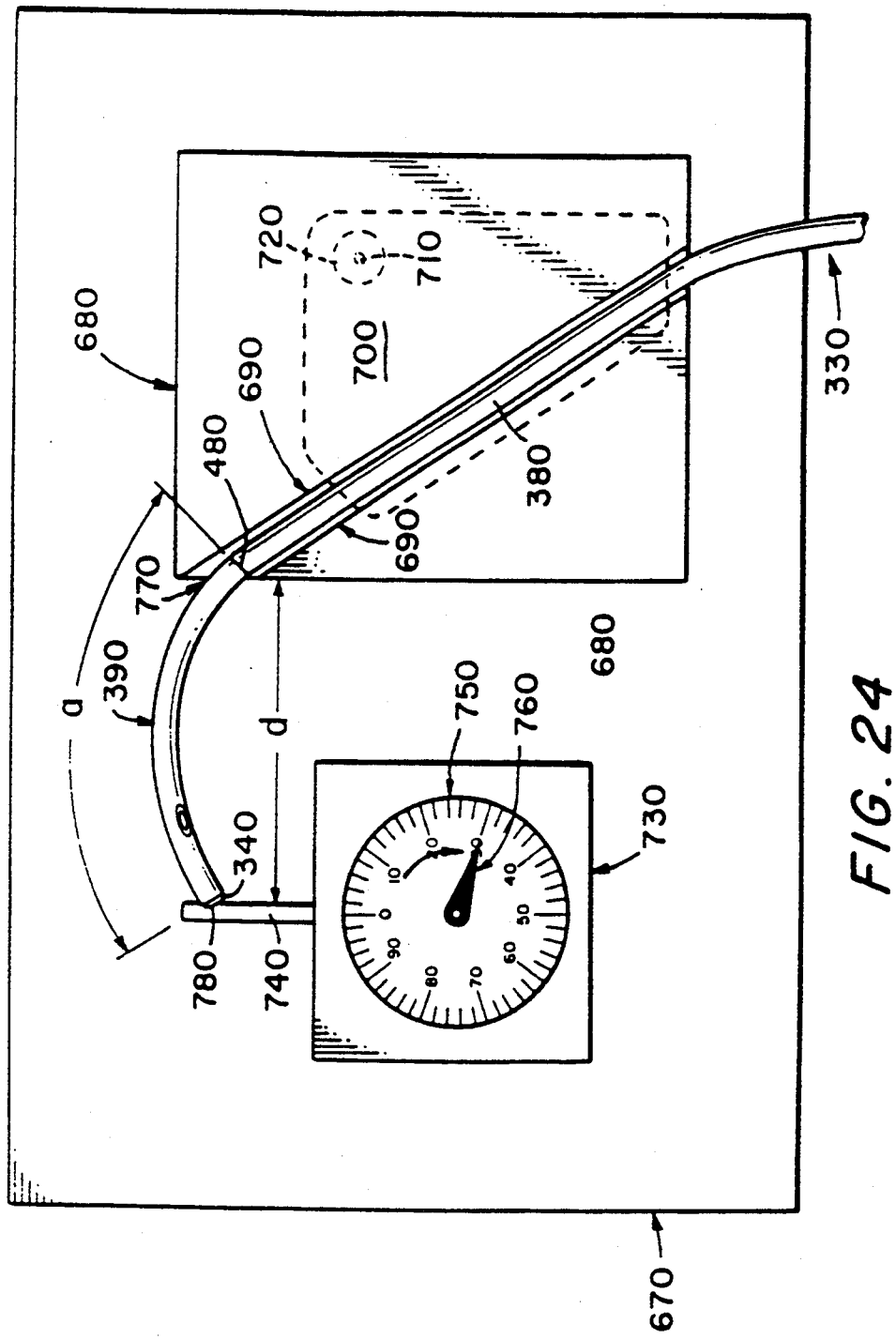
FIG. 24 is a diagram showing the method and apparatus for determining the force exerted by the distal end of the catheter of the invention.

FIG. 24 shows an apparatus for standardizing the amount of force generated by the tip 340 pressing against the myocardium when the catheter 330 is in place. This apparatus and the method for using it are equally applicable to the other embodiments of the catheter of the present invention.

A catheter force gauge 70 is shown, and includes a catheter receiving block 680 mounted thereon, with the block 680 including a groove 690 for receiving the catheter 330. A clamp 700 is rotatably mounted on the block 680 at axis 710, and may be tightened by means of a threaded knob 720 or other conventional means of clamping.

A gram-force gauge 730 comprises the measuring portion of the catheter-force gauge 670, and is mounted in a fixed position relative to the block 680. The gauge 730 includes a measuring arm 740 and a dial indicator 750 of conventional design, wherein force against the arm 740 causes a pointer 760 to indicate the amount of force on the dial indicator 750.

In order to utilize the catheter force gauge 670, the know 720 is loosened, and the clamp 700 is rotated out of the way of the groove 690. The catheter 330 is then laid in the groove such that the junction 480 between the main section 380 and the tip section 390 lies just at the upper left end 770 of the groove 690. Then the clamp 700 is rotated so that it overlies the catheter 330, and the knob 720 is tightened to hold the catheter 330 tightly within the groove 690. The tip electrode 340 is then placed in a cup-shaped receptacle 780 of the arm 740. It will be understood that the length of the arc a described between the tip electrode 340 and the junction 480 must be somewhat greater than the distance d between the arm 740 and the upper left end 770 of the groove 690. In the preferred embodiment, arc a (i.e., the distance along the length of the catheter 330 between the tip electrode 340 and the junction 480) is 4 inches, and the length d is 3 inches.

Once the tip electrode is placed within the receptacle 780, the force reading will appear on the dial indicator 750. This force will depend upon the type of material utilized for the stiffener 430, as well as upon the configuration thereof, and the shape of the arc a into which the distal end of the catheter 330 is bent (i.e., the shape which it retains when not under tension). For instance, if the arc a is a fairly flat curve, such as a 30° curve, then when the tip electrode 340 has been fitted into the receptacle 780, a reading of, for example, 22 g, may appear on the dial indicator 750, as shown in FIG. 4. However, if the distal end of the catheter 330 is bent into a tighter curve-such as a 40° arc-then when the catheter 330 is placed in the gauge 670, a lower reading on the dial indicator 750 will result, since there is less tension required to be placed on the elastic stiffener 430 in order to place the tip electrode 340 into the receptacle 780. In this manner, forces may be measured for a variety of stiffeners and radii of curvatures of the distal end of the catheter. Once a physician is acquainted with the approximate amount of curvature for a given configuration of catheter 330 which is necessary to generate the desired force, such as 22 g of force, he or she will be able to estimate the amount of force being exerted against the endocardium by the tip electrode 340 when the catheter 330 is inserted into an in vivo heart, by observing the distal end of the catheter 330 on the fluoroscope.

Figure 25:
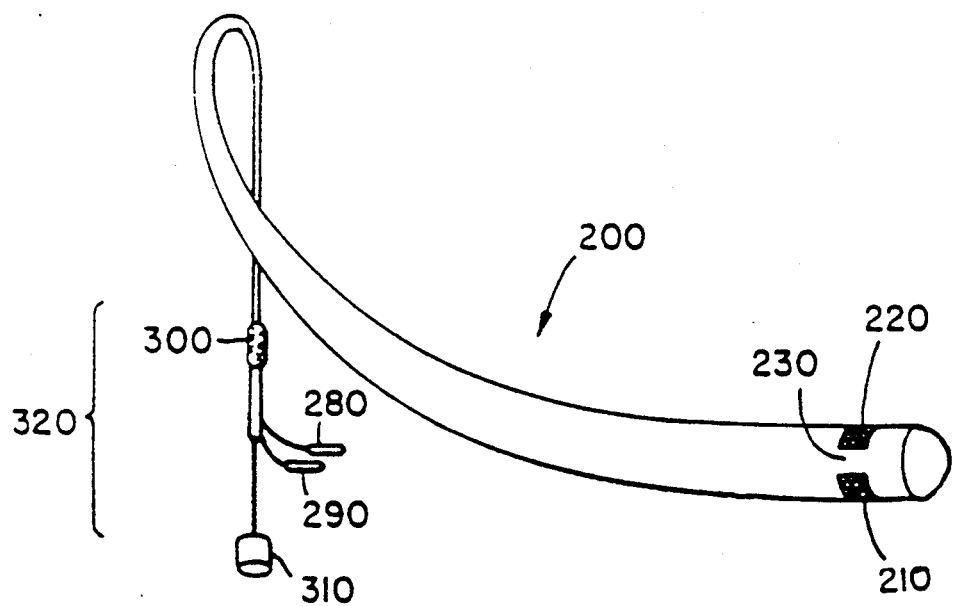
FIG. 25 shows an alternative embodiment of the device of FIG. 17.

A variation on the embodiment of FIG. 17 is shown in FIG. 25, wherein corresponding reference numerals are used to refer to identical structures. FIG. 25 represents an embodiment wherein the MAP electrodes 240 and 250 are not used. An equivalent result may be achieved by utilizing the embodiment shown in FIG. 17, but without utilizing the MAP electrodes 240 and 250. Applicant has learned that the placement of the pacing electrodes 210 and 220 (as shown in both FIGS. 17 and 25) near the tip 230 of the catheter 200 results in a lower threshold voltage being required to pace an in vivo heart. Because of this, less power is required to pace the heart, resulting in several advantages, including the important features that a battery of a portable pacemaker will last considerably longer with the present invention, and that a lower-potential pacing signal is less likely to lead to unwanted artefacts. Such a system should also lead to lessened tissue trauma.

Several structural features seem to contribute to the lowering of the pacing threshold, including the feature that the pacing electrodes 210 and 220 are positioned substantially on opposite sides of the catheter tip 230, or at least displaced by about a ninety degrees around the circumference. Applicant believes that the resulting dipole contributes to the lower pacing threshold; thus, other configurations which result in such a dipole may also be used. In addition, the relatively small size of the pacing electrodes 210 and 220 leads to higher surface current density for a given voltage, again allowing for the lower pacing threshold. Various shapes of the pacing electrodes may be used (such as diagonals, squares, straight electrodes parallel or perpendicular to the catheter body, etc.), the more important characteristics being their small size and their placement relative to the catheter tip and to one another.

In applications where the tip 230 of the catheter (or the tip electrode 240 as in FIG. 17) is pressed against the endomyocardium, the pacing electrodes 210 and 220 may strategically be placed a few millimeters from the very tip of the catheter (or the tip electrode 240), where contact is made with the heart tissue. As discussed above, the pressure of the tip of the catheter on the heart tissue leads to a depolarization in the vicinity of the pressure, which causes the tissue to be more refractory, i.e. less responsive to excitation. Thus, it is advantageous to locate the pacing electrodes 210 and 220 away from the region of depolarization and toward less refractory, more responsive myocardium, to further contribute to the lowering of the pacing threshold. Where proximity to the catheter tip of the pacing electrodes is desired, this will lead to a balance between locating the electrodes as close to the catheter tip as possible, and displacing them from the immediate region of depolarization.

The foregoing description is set forth for the purpose of illustrating the present invention. However, it should be apparent that numerous changes can be made in the invention without departing from the scope thereof, as set forth in the appended claims.

I claim:

1. A system for pacing a heart comprising
a source of a cardiac pacing signal,
a catheter body having a distal tip,
a first electrode carried on the catheter body at a first distance of two to six millimeters from the distal tip,
a second electrode carried on the catheter body at a second distance of two to six millimeters from the distal tip and also being located substantially opposite to the first electrode, and
means connecting the signal source to the first and second electrodes for conveying a cardiac pacing signal to the first and second electrodes.

2. A catheter according to claim 1 wherein the first and second distances are substantially equal.

3. A catheter according to claim 1 wherein the first and second electrodes form a dipole.

* * * * *